United States Patent
Fäcke et al.

(10) Patent No.: US 9,921,473 B2
(45) Date of Patent: Mar. 20, 2018

(54) AROMATIC GLYCOL ETHERS AS WRITING MONOMERS IN HOLOGRAPHIC PHOTOPOLYMER FORMULATIONS

(71) Applicant: Covestro Deutschland AG, Leverkusen (DE)

(72) Inventors: Thomas Fäcke, Leverkusen (DE); Friedrich-Karl Bruder, Krefeld (DE); Thomas Rölle, Leverkusen (DE); Marc-Stephan Weiser, Leverkusen (DE); Dennis Hönel, Zülpich-Wichterich (DE); Horst Berneth, Leverkusen (DE); Günther Walze, Leverkusen (DE); Rainer Hagen, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/306,272

(22) PCT Filed: Mar. 24, 2015

(86) PCT No.: PCT/EP2015/056178
§ 371 (c)(1),
(2) Date: Oct. 24, 2016

(87) PCT Pub. No.: WO2015/161969
PCT Pub. Date: Oct. 29, 2015

(65) Prior Publication Data
US 2017/0045816 A1    Feb. 16, 2017

(30) Foreign Application Priority Data

Apr. 25, 2014 (EP) .................................... 14165956

(51) Int. Cl.
*G03H 1/02* (2006.01)
*G03F 7/035* (2006.01)
(Continued)

(52) U.S. Cl.
CPC ............ *G03F 7/001* (2013.01); *C07C 69/017* (2013.01); *C07C 69/54* (2013.01); *C07C 69/612* (2013.01);
(Continued)

(58) Field of Classification Search
None
See application file for complete search history.

(56) References Cited

U.S. PATENT DOCUMENTS 4,994,347 A    2/1991  Smothers
5,260,149 A *  11/1993 Monroe ................. G03F 7/027
                                                   359/3
(Continued)

FOREIGN PATENT DOCUMENTS

EP    0223587 A1   5/1987
EP    1674940 A1   6/2006
(Continued)

OTHER PUBLICATIONS

Buruiana, T., et al., "Synthesis and Properties of Liqued Crystalline Urethane Methacrylates for Dental Composite Applications", Journal of Polymer Science Part A: Polymer Chemistry, vol. 49, No. 12, (2011), pp. 2615-2626.
(Continued)

*Primary Examiner* — Martin Angebranndt
(74) *Attorney, Agent, or Firm* — Drinker Biddle & Reath LLP

(57) ABSTRACT

The invention relates to a photopolymer formulation comprising specific aromatic glycol ethers as writing monomers, matrix polymers and a photoinitiator. The invention further provides an unexposed holographic medium obtainable using an inventive photopolymer formulation, and an exposed holographic medium obtainable by exposing a hologram into an inventive unexposed holographic medium.

(Continued)

Figure 1:
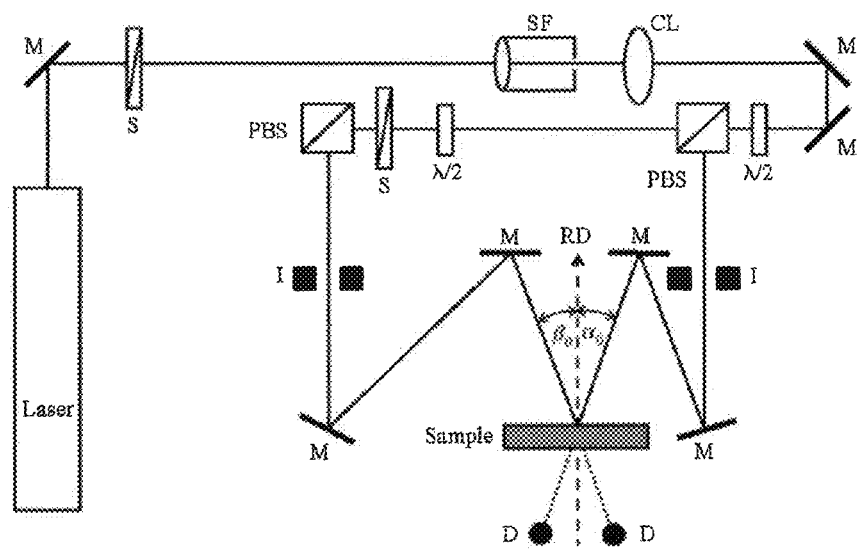

The invention likewise provides a visual display comprising an inventive exposed holographic medium, for the use of an inventive exposed holographic medium for production of chip cards, identification documents, 3D images, product protection labels, labels, banknotes or holographic optical elements, and specific aromatic glycol ethers.

15 Claims, 2 Drawing Sheets

(51) Int. Cl.
*G03F 7/032* (2006.01)
*G03F 7/028* (2006.01)
*C07C 69/612* (2006.01)
*G03F 7/00* (2006.01)
*C08F 290/06* (2006.01)
*G11B 7/24044* (2013.01)
*C07C 69/017* (2006.01)
*C07C 69/54* (2006.01)
*C07C 271/16* (2006.01)

(52) U.S. Cl.
CPC ........ *C07C 271/16* (2013.01); *C08F 290/062* (2013.01); *C08F 290/067* (2013.01); *G03F 7/028* (2013.01); *G03F 7/035* (2013.01); *G03H 1/0248* (2013.01); *G11B 7/24044* (2013.01); *G03H 2001/0264* (2013.01); *G03H 2260/12* (2013.01)

(56) References Cited

U.S. PATENT DOCUMENTS

| | | | |
|---|---|---|---|
| 6,627,354 B1* | 9/2003 | Chandross | G03F 7/001 359/3 |
| 8,710,113 B2* | 4/2014 | Eckert | A61K 6/0023 520/1 |
| 9,057,946 B2 | 6/2015 | Fäcke et al. | |
| 9,057,950 B2 | 6/2015 | Rölle et al. | |
| 9,098,065 B2 | 8/2015 | Hönel et al. | |
| 9,146,456 B2 | 9/2015 | Berneth et al. | |
| 2005/0058911 A1* | 3/2005 | Takeyama | G03F 7/001 430/1 |
| 2006/0172090 A1* | 8/2006 | Syundo | C09K 19/2007 428/1.1 |
| 2008/0102378 A1* | 5/2008 | Cole | G03H 1/02 430/2 |
| 2009/0062419 A1* | 3/2009 | Stockel | C08G 18/4252 522/109 |
| 2009/0310196 A1* | 12/2009 | Shimizu | G03H 1/02 359/3 |
| 2010/0036013 A1 | 2/2010 | Roelle et al. | |
| 2012/0219884 A1* | 8/2012 | Weiser | G03F 7/001 430/2 |

FOREIGN PATENT DOCUMENTS

| | | | |
|---|---|---|---|
| EP | 2401998 A1 | | 1/2012 |
| JP | 63-107954 | * | 5/1988 |
| JP | 09-272707 | * | 10/1997 |
| JP | 2008-001640 | * | 1/2008 |
| JP | 2012-111787 | * | 6/2012 |
| JP | 2015-040224 | * | 3/2015 |
| WO | WO-2008125199 A1 | | 10/2008 |
| WO | WO-2008125229 A1 | | 10/2008 |
| WO | WO-2011095442 A1 | | 8/2011 |
| WO | WO-2012020061 A1 | | 2/2012 |
| WO | WO-2012062655 A2 | | 5/2012 |
| WO | WO-2012062658 A1 | | 5/2012 |

OTHER PUBLICATIONS

International Search Report for PCT/EP2015/056178 dated Jun. 17, 2015.

* cited by examiner

AROMATIC GLYCOL ETHERS AS WRITING MONOMERS IN HOLOGRAPHIC PHOTOPOLYMER FORMULATIONS

CROSS-REFERENCE TO RELATED APPLICATIONS

This application is a national stage application (under 35 U.S.C. § 371) of PCT/EP2015/056178, filed Mar. 24, 2015, which claims benefit of European Application No. 14165956.5, filed Apr. 25, 2014, both of which are incorporated herein by reference in their entirety.

The invention relates to a photopolymer formulation comprising writing monomers, matrix polymers and a photoinitiator. The invention further provides an unexposed holographic medium obtainable using an inventive photopolymer formulation, and an exposed holographic medium obtainable by exposing a hologram into an inventive unexposed holographic medium. The invention likewise provides a visual display comprising an inventive exposed holographic medium, for the use of an inventive exposed holographic medium for production of chip cards, identification documents, 3D images, product protection labels, labels, banknotes or holographic optical elements, and specific aromatic glycol ethers.

BACKGROUND OF THE INVENTION

For the uses of photopolymer formulations, the crucial role is played by the refractive index contrast Δn produced in the photopolymer by the holographic exposure. In holographic exposure, the interference field of signal light beam and reference light beam (that of two planar waves in the simplest case) is mapped into a refractive index grating by the local photopolymerization of, for example, high-refractive acrylates at loci of high intensity in the interference field. The refractive index grating in the photopolymer (the hologram) contains all the information of the signal light beam. By illuminating the hologram with only the reference light beam, the signal can then be reconstructed. The strength of the signal thus reconstructed relative to the strength of the incident reference light is called the diffraction efficiency, DE in what follows.

In the simplest case of a hologram resulting from the superposition of two plane waves, the DE is the ratio of the intensity of the light diffracted on reconstruction to the sum total of the intensities of incident reference light and diffracted light. The higher the DE, the greater the efficiency of a hologram with regard to the amount of reference light needed to visualize the signal with a fixed brightness.

High-refractive acrylates are capable of producing refractive index gratings with high amplitude between regions with low refractive index and regions with high refractive index, and hence of enabling holograms with high DE and high Δn in photopolymer formulations. It should be noted here that DE depends on the product of Δn and the photopolymer layer thickness d. The breadth of the angle range at which the hologram is visibly (reconstructed), for example under monochromatic illumination, depends solely on the layer thickness d.

On illumination of the hologram with white light, for example, the breadth of the spectral range which can contribute to the reconstruction of the hologram likewise depends solely on the layer thickness d. The smaller d is, the greater the respective breadths of acceptance. Therefore, if the intention is to produce bright and readily visible holograms, the aim is a high Δn and a low thickness d, so as to maximize DE. This means that, the higher the Δn, the more freedom is achieved to configure the layer thickness d for bright holograms without loss of DE. Therefore, the optimization of Δn is of major importance in the optimization of photopolymer formulations (P. Hariharan, Optical Holography, 2nd Edition, Cambridge University Press, 1996).

WO 2008/125229 discloses photopolymer formulations comprising mono- and difunctional writing monomers of high molecular weight. Media made from these formulations can be used to write reflection holograms of good suitability for data storage, for example. However, problems occur in the production and processing of the formulations: For instance, the writing monomers present have a high viscosity or high $T_G$ values ($T_G$=glass transition temperature). This means that it is difficult to achieve homogeneous distribution of the writing monomers in the photopolymer formulation and a medium produced therefrom. Moreover, when the known formulations are used, writing monomer agglomerates can be formed in the polymer matrix, which considerably impairs the quality of the media or the holograms exposed therein. In such cases, the holographic materials become hazy.

A particular form of holograms is that of transmission holograms, a feature of which is that, in the course of production of the holograms, the reference beam and the object beam irradiate the holographic medium from the same side. Transmission holograms find various uses. Particular mention should be made here of the light guide as diffractive optical element. Such an optical element can be used in demanding applications such as spectroscopy or astronomy. They are likewise suitable for use in electronic displays, for example in 3D displays.

Because of the geometry of the interfering object and signal beams, the lattice spacing in transmission holograms is large compared to reflection holograms. According to the wavelength, it may be between 500-1000 nm. Since the mechanism of hologram formation in the photopolymer is based on the diffusion of the writing monomers, there is a need for writing monomers which can diffuse far enough with the large lattice spacing customary for transmission holograms. However, this is a prerequisite for being able to enable a high refractive index contrast (Δn). The photopolymers known from the field of reflection holograms are frequently unsuitable for this purpose, or do not lead to a sufficiently high refractive index contrast.

WO 2012/020061 describes specific writing monomers containing (meth)acrylate groups and based on thioethers, and also photopolymer formulations and media comprising them, especially for recording transmission holograms. However, the process used to prepare the writing monomers has disadvantages: Thus, in a first step, epoxides and thiols are reacted under catalysis to give hydroxy-functional thioethers, which are then reacted in a second step with isocyanate-functional acrylates. However, the reaction of the thiols is a comparatively slow reaction, and full conversion of the usually highly odorous reactants is difficult to achieve. The handling of these materials and the cleaning of reaction vessels in the production environment also entail a relatively high level of cost and inconvenience. Moreover, unconverted free thiols inhibit free-radical polymerization, and so it would be desirable to identify alternatives to the products described that can be prepared in a thiol-free manner.

Moreover, a disadvantage of the writing monomers of WO 2012/020061 and of WO 2008/125199 is that they have high viscosity and are pasty materials. This makes it difficult to produce photopolymer formulations, since efficient, rapid, homogeneous mixing of the components is achievable. Moreover, these high-viscosity writing monomers are difficult to filter and generally disadvantageous to handle. Moreover, it may also be necessary to use organic solvents, which is disadvantageous for reasons of occupational safety and environmental protection. Furthermore, it is disadvantageous to use solvents in production of holographic media, especially with high layer thicknesses, since they can be removed, for example, from media in the form of films only with a relatively high level of complexity, in which case, however, there can again be impairment of the quality, for instance in the form of surface defects. However, such defects are unacceptable in many cases, since the media can then no longer achieve the high-precision optical functions for which they are intended.

Moreover, it is generally advantageous in the development of photopolymer formulations when the writing monomers have a high solubility in the further components. Thus, in this case, the quantitative ratios of the components in the formulation can be varied within a relatively wide ranges, which considerably eases adaptation to specific applications or actually makes it possible at all.

BRIEF SUMMARY OF THE INVENTION

It was therefore an object of the present invention to provide a photopolymer formulation of the type specified at the outset, in which the writing monomer present dissolves quickly and easily without addition of solvents. Furthermore, it should be possible to prepare the writing monomer present without use of thiols. Finally, it should be possible to obtain, from the photopolymer formulation, holographic media having low haze, i.e. having a haze of less than 5% at a photopolymer layer thickness of >6 μm, and into which transmission holograms with a high refractive index contrast ($\Delta n$) of more than 0.02 can be exposed.

This object is achieved by a photopolymer formulation comprising
A) as writing monomer at least one aromatic glycol ether of the general formula (I)

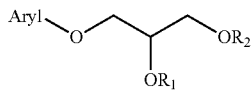

(I)

in which aryl is a substituted or unsubstituted aromatic radical, and
$R_1$ and $R_2$ are each independently a radical of the formula (II) or (III)

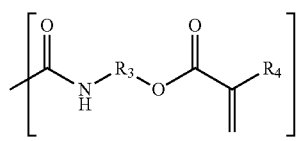

(II)

(III)

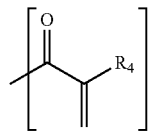

in which
$R_3$ is an organic radical which has up to 6 carbon atoms and may contain oxygen and/or sulphur atoms, and
$R_4$ is a radical selected from the group of —H, —CH$_3$;
B) matrix polymers;
C) a photoinitiator.

It has been found that, surprisingly, with the aid of the inventive photopolymer formulations, holographic media especially suitable for recording transmission holograms are obtainable. These media have low haze and additionally also give a high refractive index contrast ($\Delta n$). Moreover, the writing monomers present can be prepared without use of thiols and can be dissolved in the formulation quickly and without addition of solvents.

DETAILED DESCRIPTION OF THE INVENTION

The compounds of the formula (I) can be prepared, for example, in a two-stage process. In this process, in a first step, a mono- to bifunctional aryl glycidyl ether can first be reacted with (meth)acrylic acid. The addition in the presence of suitable catalysts, for example phosphines, phosphonium compounds, Brønsted acids or amines is preferably effected on the less sterically hindered side of the oxirane, such that more secondary than primary alcohols are formed. Subsequently, the alcohols formed can be added onto isocyanatoalkyl (meth)acrylate, giving predominantly compounds with $R_1$=(meth)acrylic acid and $R_2$=carbonylaminoalkyl (meth)acrylate. The formula scheme which follows shows the synthesis strategy once again.

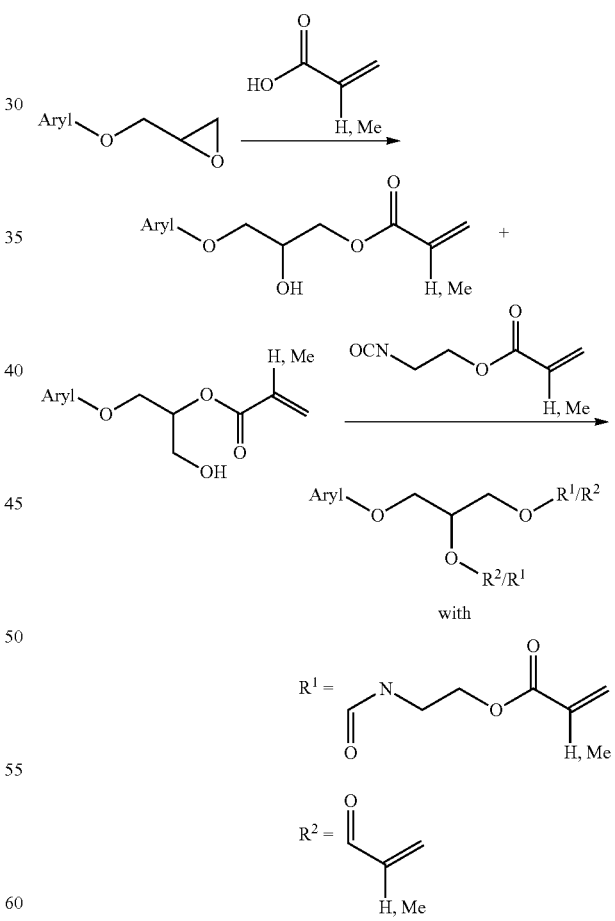

It is likewise possible to use specific catalysts which affect the regioselectivity of the addition of the (meth)acrylic acid onto the epoxide. Thus, it is possible using cobalt(III) complexes as catalysts to prepare exclusively secondary alcohols (see A. Bukowska et al., Journal of Molecular Catalysis A: Chemical 225 (2005) 7-10 and the literature cited therein). It is thus also possible to obtain regioisomerically pure products.

In an advantageous embodiment, in the compound of the formula (I), the aryl radical comprises 5 to 21, preferably 5 to 18, further preferably 6 to 16 and more preferably 6 to 12 and most preferably 6 to 10 carbon atoms and/or heteroatoms in the aromatic system.

It is likewise advantageous when, in the compound of the formula (I), the aryl radical is substituted by 1 to 5 and preferably 1 to 3 identical or different substituents selected from the group of n-alkyl, branched alkyl, alkyloxy, phenyl, benzyl, phenylalkyl, naphthyl, methylthiyl, ethylthiyl, alkylthiyl, alkylthioalkyl, phenoxy, phenylthiyl, napthylthiyl, fluorine, chlorine, bromine and/or iodine, and preferably by 1 to 3 identical or different substituents selected from the group of methyl, ethyl, thiomethyl, methoxy, phenyl.

It is most preferable when, in the compound of the formula (I), the aryl radical is selected from the group of phenyl, methylphenyl, ethylphenyl, thiomethylphenyl, methoxyphenyl, biphenyl and naphthyl.

It is also advantageous when $R_3$ is a radical selected from the group of —$CH_2$—, —$CH_2CH_2$—, $CH(CH_3)CH_2$—, —$CH_2CH(CH_3)$—, —$CH_2CH_2CH_2$—, —$CH_2CH_2CH_2CH_2$—, —$CH_2CHOCH_2CH_2$—, —$CH_2CH_2OCH_2CH_2OCH_2CH_2$— and preferably a radical selected from the group of —$CH_2CH_2$—, —$CH(CH_3)CH_2$—, —$CH_2CH(CH_3)$—, —$CH_2CH_2CH_2CH_2$—, and most preferably —$CH_2CH_2$—.

In a further embodiment, the $R_1$ radical is a radical of the formula (II) and the $R_2$ radical is a radical of the formula (III), where the $R_3$ radical may especially be a —$CH_2CH_2$— radical. Alternatively, the $R_1$ radical may be a radical of the formula (III) and the $R_2$ radical a radical of the formula (II), where the $R_3$ radical may especially be a —$CH_2CH_2$— radical.

Matrix polymers B) used may be amorphous thermoplastics, for example polyacrylates, polymethylmethacrylates or copolymers of methyl methacrylate, methacrylic acid or other alkyl acrylates and alkyl methacrylates, and also acrylic acid, for example polybutyl acrylate, and also polyvinyl acetate and polyvinyl butyrate, the partially hydrolysed derivatives thereof, such as polyvinyl alcohols, and copolymers with ethylenes and/or further (meth)acrylates, gelatins, cellulose esters and cellulose ethers such as methyl cellulose, cellulose acetobutyrate, silicones, for example polydimethylsilicone, polyurethanes, polybutadienes and polyisoprenes, and also polyethylene oxides, epoxy resins, especially aliphatic epoxy resins, polyamides, polycarbonates and the systems cited in U.S. Pat. No. 4,994,347A and therein.

It is particularly preferable, however, when the matrix polymers are polyurethanes.

It is particularly preferable when the matrix polymers have been crosslinked. It is especially preferably when the matrix polymers have been three-dimensionally crosslinked. Epoxy resins may be canonically intercrosslinked. In addition, it is also possible to use acids/anhydrides, amines, hydroxyalkyl amides and thiols as crosslinkers.

Silicones can be crosslinked either as one-component systems through condensation in the presence of water (and optionally under Brønsted acid catalysis) or as two-component systems by addition of silicic esters or organotin compounds. Likewise possible is the hydrosilylations in vinyl silane systems.

Unsaturated compounds, for example acryloyl-functional polymers or unsaturated esters, can be crosslinked with amines or thiols. Cationic vinyl ether polymerization is also possible.

It is most preferable when the matrix polymers are crosslinked and especially three-dimensionally crosslinked polyurethanes.

The polyurethanes are obtainable especially by reaction of at least one polyisocyanate component a) with at least one isocyanate-reactive component b).

The polyisocyanate component a) comprises at least one organic compound having at least two NCO groups. These organic compounds may especially be monomeric di- and triisocyanates, polyisocyanates and/or NCO-functional prepolymers. The polyisocyanate component a) may also contain or consist of mixtures of monomeric di- and triisocyanates, polyisocyanates and/or NCO-functional prepolymers.

Monomeric di- and triisocyanates used may be any of the compounds that are well known per se to those skilled in the art, or mixtures thereof. These compounds may have aromatic, araliphatic, aliphatic or cycloaliphatic structures. The monomeric di- and triisocyanates may also comprise minor amounts of monoisocyanates, i.e. organic compounds having one NCO group.

Examples of suitable monomeric di- and triisocyanates are butane 1,4-diisocyanate, pentane 1,5-diisocyanate, hexane 1,6-diisocyanate (hexamethylene diisocyanate, HDI), 2,2,4-trimethylhexamethylene diisocyanate and/or 2,4,4-trimethylhexamethylene diisocyanate (TMDI), isophorone diisocyanate (IPDI), 1,8-diisocyanato-4-(isocyanatomethyl)octane, bis(4,4'-isocyanatocyclohexyl)methane and/or bis(2',4-isocyanatocyclohexyl)methane and/or mixtures thereof having any isomer content, cyclohexane 1,4-diisocyanate, the isomeric bis(isocyanatomethyl)cyclohexanes, 2,4- and/or 2,6-diisocyanato-1-methylcyclohexane (hexahydrotolylene 2,4- and/or 2,6-diisocyanate, $H_6$-TDI), phenylene 1,4-diisocyanate, tolylene 2,4- and/or 2,6-diisocyanate (TDI), naphthylene 1,5-diisocyanate (NDI), diphenylmethane 2,4'- and/or 4,4'-diisocyanate (MDI), 1,3-bis (isocyanatomethyl)benzene (XDI) and/or the analogous 1,4 isomers or any desired mixtures of the aforementioned compounds.

Suitable polyisocyanates are compounds which have urethane, urea, carbodiimide, acylurea, amide, isocyanurate, allophanate, biuret, oxadiazinetrione, uretdione and/or iminooxadiazinedione structures and are obtainable from the aforementioned di- or triisocyanates.

More preferably, the polyisocyanates are oligomerized aliphatic and/or cycloaliphatic di- or triisocyanates, it being possible to use especially the above aliphatic and/or cycloaliphatic di- or triisocyanates.

Very particular preference is given to polyisocyanates having isocyanurate, uretdione and/or iminooxadiazinedione structures, and biurets based on HDI or mixtures thereof.

Suitable prepolymers contain urethane and/or urea groups, and optionally further structures formed through modification of NCO groups as specified above. Prepolymers of this kind are obtainable, for example, by reaction of the abovementioned monomeric di- and triisocyanates and/or polyisocyanates a1) with isocyanate-reactive compounds b1).

Isocyanate-reactive compounds b1) used may be alcohols, amino or mercapto compounds, preferably alcohols. These may especially be polyols. Most preferably, isocyanate-reactive compounds b1) used may be polyester polyols, polyether polyols, polycarbonate polyols, poly(meth)acrylate polyols and/or polyurethane polyols.

Suitable polyester polyols are, for example, linear polyester diols or branched polyester polyols, which can be obtained in a known manner by reaction of aliphatic, cycloaliphatic or aromatic di- or polycarboxylic acids or anhydrides thereof with polyhydric alcohols of OH functionality ≥2. Examples of suitable di- or polycarboxylic acids are polybasic carboxylic acids such as succinic acid, adipic acid, suberic acid, sebacic acid, decanedicarboxylic acid, phthalic acid, terephthalic acid, isophthalic acid, tetrahydrophthalic acid or trimellitic acid, and acid anhydrides such as phthalic anhydride, trimellitic anhydride or succinic anhydride, or any desired mixtures thereof. The polyester polyols may also be based on natural raw materials such as castor oil. It is likewise possible that the polyester polyols are based on homo- or copolymers of lactones, which can preferably be obtained by addition of lactones or lactone mixtures, such as butyrolactone, ε-caprolactone and/or methyl-ε-caprolactone onto hydroxy-functional compounds such as polyhydric alcohols of OH functionality≥2, for example of the abovementioned type.

Examples of suitable alcohols are all polyhydric alcohols, for example the $C_2$-$C_{12}$ diols, the isomeric cyclohexanediols, glycerol or any desired mixtures thereof.

Suitable polycarbonate polyols are obtainable in a manner known per se by reaction of organic carbonates or phosgene with diols or diol mixtures.

Suitable organic carbonates are dimethyl, diethyl and diphenyl carbonate.

Suitable diols or mixtures comprise the polyhydric alcohols of OH functionality≥2 mentioned per se in the context of the polyester segments, preferably butane-1,4-diol, hexane-1,6-diol and/or 3-methylpentanediol. It is also possible to convert polyester polyols to polycarbonate polyols.

Suitable polyether polyols are polyacidition products, optionally of blockwise structure, of cyclic ethers onto OH- or NH-functional starter molecules.

Suitable cyclic ethers are, fix example, styrene oxides, ethylene oxide, propylene oxide, tetrahydrofuran, butylene oxide, epichlorohydrin, and any desired mixtures thereof.

Starters used may be the polyhydric alcohols of OH functionality≥2 mentioned per se in the context of the polyester polyols, and also primary or secondary amines and amino alcohols.

Preferred polyether polyols are those of the aforementioned type based exclusively on propylene oxide, or random or block copolymers based on propylene oxide with further 1-alkylene oxides. Particular preference is given to propylene oxide homopolymers and random or block copolymers containing oxyethylene, oxypropylene and/or oxybutylene units, where the proportion of the oxypropylene units based on the total amount of all the oxyethylene, oxypropylene and oxybutylene units amounts to at least 20% by weight, preferably at least 45% by weight. Oxypropylene and oxybutylene here encompasses all the respective linear and branched $C_3$ and $C_4$ isomers.

Additionally suitable as constituents of the polyol component b1), as polyfunctional, isocyanate-reactive compounds, are also low molecular weight (i.e. with molecular weights≤500 g/mol), short-chain (i.e. containing 2 to 20 carbon atoms), aliphatic, araliphatic or cycloaliphatic di-, tri- or polyfunctional alcohols.

These may, for example, in addition to the abovementioned compounds, be neopentyl glycol, 2-ethyl-2-butylpropanediol, trimethylpentanediol, positionally isomeric diethyloctanediols, cyclohexanediol, 1,4-cyclohexanedimethanol, 1,6-hexanediol, 1,2- and 1,4-cyclohexanediol, hydrogenated bisphenol A, 2,2-bis(4-hydroxycyclohexyl)propane or 2,2-dimethyl-3-hydroxypropionic acid, 2,2-dimethyl-3-hydroxypropionate. Examples of suitable triols are trimethylolethane, trimethylolpropane or glycerol. Suitable higher-functionality alcohols are di(trimethylolpropane), pentaerythritol, dipentaerythritol or sorbitol.

It is especially preferable when the polyol component is a difunctional polyether, polyester, or a polyether-polyester block copolyester or a polyether-polyester block copolymer having primary OH functions.

It is likewise possible to use amines as isocyanate-reactive compounds b1). Examples of suitable amines are ethylenediamine, propylenediamine, diaminocyclohexane, 4,4'-dicyclohexylmethanediamine, isophoronediamine (IPDA), difunctional polyamines, for example the Jeffamines®, amine-terminated polymers, especially having number-average molar masses≤10 000 g/mol. Mixtures of the aforementioned amines can likewise be used.

It is likewise possible to use amino alcohols as isocyanate-reactive compounds b1). Examples of suitable amino alcohols are the isomeric aminoethanols, the isomeric aminopropanols, the isomeric aminobutanols and the isomeric aminohexanols, or any desired mixtures thereof.

All the aforementioned isocyanate-reactive compounds b1) can be mixed with one another as desired.

It is also preferable when the isocyanate-reactive compounds b1) have a number-average molar mass of ≥200 and ≤10 000 g/mol, further preferably ≥500 and ≤8000 g/mol and most preferably ≥800 and ≤5000 g/mol. The OH functionality of the polyols is preferably 1.5 to 6.0, more preferably 1.8 to 4.0.

The prepolymers of the polyisocyanate component a) may especially have a residual content of free monomeric di- and triisocyanates of <1% by weight, more preferably <0.5% by weight and most preferably <0.3% by weight.

It is optionally also possible that the polyisocyanate component a) contains, entirely or in part, organic compound whose NCO groups have been fully or partly reacted with blocking agents known from coating technology. Example of blocking agents are alcohols, lactams, oximes, malonic esters, pyrazoles, and amines, for example butanone oxime, diisopropylamine, diethyl malonate, ethyl acetoacetate, 3,5-dimethylpyrazole, ε-caprolactam, or mixtures thereof.

It is especially preferable when the polyisocyanate component a) comprises compounds having aliphatically bonded NCO groups, aliphatically bonded NCO groups being understood to mean those groups that are bonded to a primary carbon atom. The isocyanate-reactive component b) preferably comprises at least one organic compound having an average of at least 1.5 and preferably 2 to 3 isocyanate-reactive groups. In the context of the present invention, isocyanate-reactive groups are regarded as being preferably hydroxyl, amino or mercapto groups.

The isocyanate-reactive component may especially comprise compounds having a numerical average of at least 1.5 and preferably 2 to 3 isocyanate-reactive groups.

Suitable polyfunctional isocyanate-reactive compounds of component b) are for example the above-described compounds b1).

It is also most preferable when the polyurethanes are based on polyester C4 polyether polyols.

Photoinitiators of component C) are compounds activatable typically by means of actinic radiation, which can trigger polymerization of the writing monomers. In the case of the photoinitiators, a distinction can be made between unimolecular (type I) and bimolecular (type II) initiators. In addition, they are distinguished by their chemical nature as photoinitiators for free-radical, anionic, cationic or mixed types of polymerization.

Type I photoinitiators (Norrish type I) for free-radical photopolymerization form free radicals on irradiation through unimolecular bond scission. Examples of type I photoinitiators are triazines, oximes, benzoin ethers, benzil ketals, bisimidazoles, aroylphosphine oxides, sulphonium salts and iodonium salts.

Type II photoinitiators (Norrish type II) for free-radical polymerization consist of a dye as sensitizer and a coinitiator, and undergo a bimolecular reaction on irradiation with light matched to the dye. First of all, the dye absorbs a photon and transfers energy from an excited state to the coinitiator. The latter releases the polymerization-triggering free radicals through electron or proton transfer or direct hydrogen abstraction.

In the context of this invention, preference is given to using type II photoinitiators.

Photoinitiator systems of this kind are described in principle in EP 0 223 587 A and consist preferably of a mixture of one or more dyes with ammonium alkylarylborate(s).

Suitable dyes which, together with an ammonium alkylarylborate, form a type II photoinitiator are the cationic dyes described in WO 2012062655, in combination with the anions likewise described therein.

Cationic dyes are preferably understood to mean those from the following classes: acridine dyes, xanthene dyes, thioxanthene dyes, phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, externally cationic merocyanine dyes, externally cationic neutrocyanine dyes, zeromethine dyes—especially naphtholactam dyes, streptocyanine dyes. Dyes of this kind are described, for example, in H. Berneth in Ullmann's Encyclopedia of Industrial Chemistry, Azine Dyes, Wiley-VCH Verlag, 2008, H. Berneth in Ullmann's Encyclopedia of Industrial Chemistry, Methine Dyes and Pigments, Wiley-VCH Verlag, 2008, T. Gessner, U. Mayer in Ullmann's Encyclopedia of Industrial Chemistry, Triarylmethane and Diarylmethane Dyes, Wiley-VCH Verlag, 2000.

Particular preference is given to phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, zeromethine dyes—especially naphtholactam dyes, streptocyanine dyes.

Examples of cationic dyes are Astrazon Orange G, Basic Blue 3, Basic Orange 22, Basic Red 13, Basic Violet 7, Methylene Blue, New Methylene Blue, Azure A, 2,4-diphenyl-6-(4-methoxyphenyl)pyrylium, Safranin O, Astraphloxin, Brilliant Green, Crystal Violet, Ethyl Violet and thionine.

Preferred anions are especially $C_8$- to $C_{25}$-alkanesulphonate, preferably $C_{13}$- to $C_{25}$-alkanesulphonate, $C_3$- to $C_{18}$-perfluoroalkanesulphonate, $C_4$- to $C_{18}$-perfluoroalkanesulphonate bearing at least 3 hydrogen atoms in the alkyl chain, $C_9$- to $C_{25}$-alkanoate, $C_9$- to $C_{25}$-alkenoate, $C_8$- to $C_{25}$-alkylsulphate, preferably $C_{13}$- to $C_{25}$-alkylsulphate, $C_8$- to $C_{25}$-alkenylsulphate, preferably $C_{13}$- to $C_{25}$-alkenylsulphate, $C_3$- to $C_{18}$-perfluoroalkylsulphate, $C_4$- to $C_{18}$-perfluoroalkylsulphate bearing at least 3 hydrogen atoms in the alkyl chain, polyether sulphates based on at least 4 equivalents of ethylene oxide and/or 4 equivalents of propylene oxide, bis($C_4$- to $C_{25}$-alkyl, $C_5$- to $C_7$-cycloalkyl, $C_3$- to $C_8$-alkenyl or $C_7$- to $C_{11}$-aralkyl)sulphosuccinate, bis-$C_2$- to $C_{10}$-alkylsulphosuccinate substituted by at least 8 fluorine atoms, $C_9$- to $C_{25}$-alkylsulphoacetates, benzenesulphonate substituted by at least one radical from the group of halogen, $C_4$- to $C_{25}$-alkyl, perfluoro-$C_1$- to $C_8$-alkyl and/or $C_1$- to $C_{12}$-alkoxycarbonyl, naphthalene- or biphenylsulphonate optionally substituted by nitro, cyano, hydroxyl, $C_1$- to $C_{25}$-alkyl, $C_1$- to $C_{12}$-alkoxy, amino, $C_1$- to $C_{12}$-alkoxycarbonyl or chlorine, benzene-, naphthalene- or biphenyldisulphonate optionally substituted by nitro, cyano, hydroxyl, $C_1$ to $C_{25}$-alkyl, $C_1$- to $C_{12}$-alkoxy, $C_1$- to $C_{12}$-alkoxycarbonyl or chlorine, benzoate substituted by dinitro, $C_6$- to $C_{25}$-alkyl, $C_4$- to $C_{12}$-alkoxycarbonyl, benzoyl, chlorobenzoyl or tolyl, the anion of naphthalenedicarboxylic acid, diphenyl ether disulphonate, sulphonated or sulphated, optionally at least monounsaturated $C_8$ to $C_{25}$ fatty acid esters of aliphatic $C_1$ to $C_8$ alcohols or glycerol, bis(sulpho-$C_2$- to $C_6$-alkyl) $C_3$- to $C_{12}$-alkanedicarboxylates, bis(sulpho-$C_2$- to $C_6$-alkyl) itaconates, (sulpho-$C_2$- to $C_6$-alkyl) $C_6$- to $C_{18}$-alkanecarboxylates, (sulpho-$C_2$- to $C_6$-alkyl) acrylates or methacrylates, triscatechol phosphate optionally substituted by up to 12 halogen radicals, an anion from the group of tetraphenylborate, cyanotriphenylborate, tetraphenoxyborate, $C_4$- to $C_{12}$-alkyltriphenylborate, wherein the phenyl or phenoxy radicals may be substituted by halogen, $C_1$- to $C_4$-alkyl and/or $C_1$- to $C_4$-alkoxy, $C_4$- to $C_{12}$-alkyltrinaphthylborate, tetra-$C_1$- to $C_{20}$-alkoxyborate, 7,8- or 7,9-dicarba-nido-undecaborate(1-) or (2-), which are optionally substituted on the boron and/or carbon atoms by one or two $C_1$- to $C_{12}$-alkyl or phenyl groups, dodecahydrodicarbadodecaborate(2-) or B—$C_1$- to $C_{12}$-alkyl-C-phenyldodecahydrodicarbadodecaborate(1-), where, in the case of polyvalent anions such as naphthalenedisulphonate, $A^-$ represents one equivalent of this anion, and where the alkane and alkyl groups may be branched and/or may be substituted by halogen, cyano, methoxy, ethoxy, methoxycarbonyl or ethoxycarbonyl.

It is also preferable when the anion $A^-$ of the dye has an AClogP in the range from 1 to 30, more preferably in the range from 1 to 12 and especially preferably in the range from 1 to 6.5. AClogP is calculated according to J. Comput. Aid. Mol. Des. 2005, 19, 453; Virtual Computational Chemistry Laboratory, http://www.vcclab.org.

Suitable ammonium alkylarylborates are, for example (Cunningham et al., RadTech '98 North America UV/EB Conference Proceedings, Chicago, Apr. 19-22, 1998): tetrabutylammonium triphenylhexylborate, tetrabutylammonium triphenylbutylborate, tetrabutylammonium trinaphthylhexylborate, tetrabutylammonium tris(4-tert-butyl)phenylbutylborate, tetrabutylammonium tris(3-fluorophenyl)hexylborate hexylborate ([191726-69-9], CGI 7460, product from BASF SE, Basle, Switzerland), 1-methyl-3-octylimidazolium dipentyldiphenylborate and tetrabutylammonium tris (3-chloro-4-methylphenyl)hexylborate ([1147315-11-4], CGI 909, product from BASF SE, Basle, Switzerland).

It may be advantageous to use mixtures of these photoinitiators. According to the radiation source used, the type and concentration of photoinitiator has to be adjusted in the manner known to those skilled in the art. Further details are described, for example, in P. K. T. Oldring (Ed.), Chemistry & Technology of UV & EB Formulations For Coatings, Inks & Paints, vol. 3, 1991, SITA Technology, London, p. 61 328.

It is most preferable when the photoinitiator comprises a combination of dyes whose absorption spectra at least partly cover the spectral range from 400 to 800 nm, with at least one coinitiator matched to the dyes.

It is also preferable when at least one photoinitiator suitable for a laser light colour selected from blue, green and red is present in the photopolymer formulation.

It is also further preferable when the photopolymer formulation contains one suitable photoinitiator each for at least two laser light colours selected from blue, green and red.

Finally, it is most preferable when the photopolymer formulation contains one suitable photoinitiator for each of the laser light colours blue, green and red.

Particularly high refractive index contrasts can be achieved when the photopolymer formulation comprises, as further writing monomer A), as well as the writing monomer of the formula (I), preferably an acrylate- or methacrylate-functional writing monomer. Particular preference is given to monofunctional writing monomers and especially to those monofunctional urethane (meth)acrylates described in US 2010/0036013 A1.

Suitable acrylate writing monomers are especially compounds of the general formula (IV)

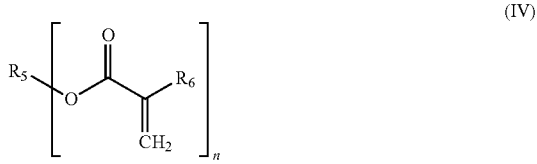

in which n≥1 and n≤4 and $R_5$ is a linear, branched, cyclic or heterocyclic organic radical which is unsubstituted or else optionally substituted by heteroatoms and/or $R_6$ is hydrogen or a linear, branched, cyclic or heterocyclic organic radical which is unsubstituted or else optionally substituted by heteroatoms. More preferably, $R_6$ is hydrogen or methyl and/or $R_5$ is a linear, branched, cyclic or heterocyclic organic radical which is unsubstituted or else optionally substituted by heteroatoms.

Acrylates and methacrylates refer, respectively, to esters of acrylic acid and methacrylic acid. Examples of acrylates and methacrylates usable with preference are phenyl acrylate, phenyl methacrylate, phenoxyethyl acrylate, phenoxyethyl methacrylate, phenoxyethoxyethyl acrylate, phenoxyethoxyethyl methacrylate, phenylthioethyl acrylate, phenylthioethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, bisphenal A diacrylate, bisphenol A dimethacrylate, and the ethoxylated analogue compounds thereof, N-carbazolyl acrylates.

Urethane acrylates are understood to mean compounds having at least one acrylic ester group and at least one urethane bond. Compounds of this kind can be obtained, for example, by reacting a hydroxy-functional acrylate or methacrylate with an isocyanate-functional compound.

Examples of isocyanate-functional compounds usable for this purpose are monoisocyanates, and the monomeric diisocyanates, triisocyanates and/or polyisocyanates mentioned under a). Examples of suitable monoisocyanates are phenyl isocyanate, the isomeric methylthiophenyl isocyanates. Di-, tri- or polyisocyanates have been mentioned above, and also triphenylmethane 4,4',4''-triisocyanate and tris(p-isocyanatophenyl) thiophosphate or derivatives thereof with urethane, urea, carbodiimide, acylurea, isocyanurate, allophanate, biuret, oxadiazinetrione, uretdione, iminooxadiazinedione structure and mixtures thereof. Preference is given to aromatic di-, tri- or polyisocyanates.

Useful hydroxy-functional acrylates or methacrylates for the preparation of urethane acrylates include, for example, compounds such as 2-hydroxyethyl (meth)acrylate, polyethylene oxide mono(meth)acrylates, polypropylene oxide mono(meth)acrylates, polyalkylene oxide mono(meth)acrylates, poly(ε-caprolactone) mono(meth)acrylates, for example Tone® M100 (Dow, Schwalbach, DE), 2-hydroxypropyl (meth)acrylate, 4-hydroxybutyl (meth)acrylate, 3-hydroxy-2,2-dimethylpropyl (meth)acrylate, hydroxypropyl (meth)acrylate, 2-hydroxy-3-phenoxypropyl acrylate, the hydroxy-functional mono-, di- or tetraacrylates of polyhydric alcohols such as trimethylolpropane, glycerol, pentaerythritol, dipentaerythritol, ethoxylated, propoxylated or alkoxylated trimethylolpropane, glycerol, pentaerythritol, dipentaerythritol or the technical mixtures thereof. Preference is given to 2-hydroxyethyl acrylate, hydroxypropyl acrylate, 4-hydroxybutyl acrylate and poly(ε-caprolactone) mono(meth)acrylate.

It is likewise possible to use the fundamentally known hydroxyl-containing epoxy (meth)acrylates having OH contents of 20 to 300 mg KOH/g or hydroxyl-containing polyurethane (meth)acrylates having OH contents of 20 to 300 mg KOH/g or acrylated polyacrylates having OH contents of 20 to 300 mg KOH/g and mixtures thereof, and mixtures with hydroxyl-containing unsaturated polyesters and mixtures with polyester(meth)acrylates or mixtures of hydroxyl-containing unsaturated polyesters with polyester (meth)acrylates.

Preference is given especially to urethane acrylates obtainable from the reaction of tris(p-isocyanatophenyl) thiophosphate and/or m-methylthiophenyl isocyanate with alcohol-functional acrylates such as hydroxyethyl (meth) acrylate, hydroxypropyl (meth)acrylate and/or hydroxybutyl (meth)acrylate.

It is likewise possible that the writing monomer comprises or consists of further unsaturated compounds such as α,β-unsaturated carboxylic acid derivatives, for example maleates, fumarates, maleimides, acrylamides, and also vinyl ethers, propenyl ethers, allyl ethers and compounds containing dicyclopentadienyl units, and also olefinically unsaturated compounds, for example styrene, α-methylstyrene, vinyltoluene and/or olefins.

In a further preferred embodiment, the photopolymer formulation additionally comprises monomeric fluorourethanes.

It is particularly preferable when the fluorourethanes comprise or consist of at least one compound of the formula (V)

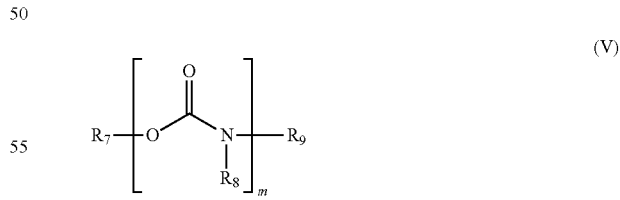

in which m≥1 and m≤8 and $R_7$, $R_8$, $R_9$ are each independently hydrogen or linear, branched, cyclic or heterocyclic organic radicals which are unsubstituted or else optionally substituted by heteroatoms, where preferably at least one of the $R_7$, $R_8$, $R_9$ radicals is substituted by at least one fluorine atom and, more preferably, $R_7$ is an organic radical having at least one fluorine atom.

It a further preferred embodiment of the invention, the photopolymer formulation comprises 10% to 89.999% by weight, preferably 20% to 70% by weight, of matrix polymers, 3% to 60% by weight, preferably 10% to 50% by weight, of writing monomers, 0.001% to 5% by weight, preferably 0.5% to 3% by weight, of photoinitiators and optionally 0% to 4% by weight, preferably 0 to 2% by weight, of catalysts, 0% to 5% by weight, preferably 0.001% to 1% by weight, of stabilizers, 0% to 40% by weight, preferably 10% to 30% by weight, of monomeric fluorourethanes and 0% to 5% by weight, preferably 0.1% to 5% by weight, of further additives, where the sum total of all the constituents is 100% by weight.

Catalysts used may be urethanization catalysts, for example organic or inorganic derivatives of bismuth, of tin, of zinc or of iron (see also the compounds specified in 2012/062658).

Particularly preferred catalysts are butyltin tris(2-ethylhexanoate), iron(III) trisacetylacetonate, bismuth(III) tris(2-ethylhexanoate) and tin(II) bis(2-ethylhexanoate). In addition, it is also possible to use sterically hindered amines as catalysts.

Stabilizers used may be
a) free-radical inhibitors, for example phenols such as para-methoxyphenol, 2,6-di-tert-butyl-4-methylphenol (ionol), and oligomeric ionols (e.g. octadecyl 3-(3,5-di-tert-butyl-4-hydroxyphenyl)propionate), and also what are called HALS amines (e.g. N,N'-bisformyl-N,N'-bis-(2,2,6,6-tetramethyl-4-piperidinyl)hexamethylenediamine), N-alkyl-HALS, N-alkoxy-HALS and N-alkoxyethyl-HALS compounds, and also phenothiazine;
b) antioxidants, for example diphosphonites, disulphides and thioethers; and/or
c) UV absorbers, such as cyanoacrylates (e.g. ethyl 2-cyano-3,3-diphenylacrylate), benzotriazoles (e.g. 2-(2H-benzotriazol-2-yl)4,6-bis(1-methyl-1-phenylethyl)phenol), benzophenones (e.g. 2-hydroxy-4-octyloxybenzophenone), benzotriazoles (e.g. 2-(2-hydroxyphenyl)benzotriazole) and oxanilides.

Further additives used may be
a) levelling aids (wetting aids), for example polyacrylates, silicones, hybrid polymers (e.g. siliconized acrylates), which are notable for adjusting surface tension, and/or
b) antistats
c) thixotropic agents
d) thickeners and/or
e) biocides.

Particular preference is given to using photopolymer formulations comprising 20% to 70% by weight of matrix polymers, 20% to 50% by weight of writing monomers, 0.001% to 5% by weight of photoinitiators, 0% to 2% by weight of catalysts, 0.001% to 1% by weight of free-radical stabilizers, optionally 10% to 30% by weight of fluorourethanes and optionally 0.1% to 5% by weight of further additives.

The invention also provides a holographic medium particularly in the form of a film comprising a photopolymer formulation of the present invention or obtainable by using a photopolymer formulation of the present invention. The invention yet further provides for the use of a photopolymer formulation of the present invention in the production of holographic media.

In one preferred embodiment of the holographic medium according to the present invention, at least one hologram has been exposed into same.

More particularly, the hologram may be a reflection, transmission, in-line, off-axis, full-aperture transfer, white light transmission, Denisyuk, off-axis reflection or edge-lit hologram, or else a holographic stereogram, and preferably a reflection, transmission or edge-lit hologram.

Possible optical functions of the holograms correspond to the optical functions of light elements such as lenses, mirrors, deflecting mirrors, filters, diffuser lenses, directed diffusion elements, diffraction elements, light guides, waveguides, projection lenses and/or masks. In addition, a plurality of such optical functions can be combined in such a hologram, for example such that the light is deflected in a different direction according to the incidence of light. For example, it is possible with such setups to build autostereoscopic or holographic electronic displays which allow a stereoscopic visual impression to be experienced without further aids, for example polarizer or shutter glasses, of the use in automobile head-up displays or head-mounted displays.

These optical elements frequently have a specific frequency selectivity according to how the holograms have been exposed and the dimensions of the hologram. This is important especially when monochromatic light sources such as LEDs or laser light are used. For instance, one hologram is required per complementary colour (RGB), in order to deflect light in a frequency-selective manner and at the same time to enable full-colour displays. Therefore, in particular display setups, several holograms have to be exposed in the medium in a super-posed manner.

In addition, by means of the inventive media, it is also possible to produce holographic images or representations, for example for personal portraits, biometric representations in security documents, or generally of images or image structures for advertising, security labels, brand protection, branding, labels, design elements, decorations, illustrations, collectable cards, images and the like, and also images which can represent digital data, including in combination with the products detailed above. Holographic images can have the impression of a three-dimensional image, but they may also represent image sequences, short films or a number of different objects according to the angle from which and the light source with which (including moving light sources) etc. they are illuminated. Because of this variety of possible designs, holograms, especially volume holograms, constitute an attractive technical solution for the abovementioned application. It is also possible to use such holograms for storage of digital data, using a wide variety of different exposure methods (shift, spatial or angular multiplexing).

The present invention also provides a process for producing a holographic medium by using a photopolymer formulation of the present invention.

Thus, the photopolymer formulations can especially be used for production of holographic media in the form of a film. In this case, a ply of a material or material composite transparent to light within the visible spectral range (transmission greater than 85% within the wavelength range from 400 to 780 nm) as carrier substrate is coated on one or both sides, and a cover layer is optionally applied to the photopolymer ply or plies.

Preferred materials or material composites for the carrier substrate are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide (PA), polymethylmethacrylate (PMMA), polyvinyl chloride, polyvinylbutyral or polydicyclopentadiene or mixtures thereof. They are more preferably based on PC, PET, PA, PMMA and CTA. Material composites may be film laminates or coextrudates. Preferred material composites are duplex and triplex films formed according to one of the schemes A/B, A/B/A or A/B/C. Particular preference is given to PC/PET, PET/PC/PET and PC/TPU (TPU=thermoplastic polyurethane).

The materials or material composites of the carrier substrate may be given an antiadhesive, antistatic, hydrophobized or hydrophilized finish on one or both sides. The modifications mentioned serve the purpose, on the side facing the photopolymer layer, of making the photopolymer ply detachable without destruction from the carrier substrate. Modification of the opposite side of the carrier substrate from the photopolymer ply serves to ensure that the inventive media satisfy specific mechanical demands which exist, for example, in the ease of processing in roll laminators, especially in roll-to-roll processes.

The invention likewise provides an optical display comprising an inventive holographic medium.

Examples of such optical displays are imaging displays based on liquid crystals, organic light-emitting diodes (OLEDs), LED display panels, microelectromechanical systems (MEMS) based on diffractive light selection, electrowetting displays (E-ink) and plasma display screens. Optical displays of this kind may be autostereoscopic and/or holographic displays, transmittive and reflective projection screens, displays with switchable restricted emission characteristics for privacy filters and bidirectional multiuser screens, virtual displays, head-up displays, head-mounted displays, illumination symbols, warning nips, signal lamps, floodlights and display panels.

In addition, the invention also provides for the use of an inventive holographic medium for production of chip cards, identity documents, 3D images, product protection labels, labels, banknotes or holographic optical elements, especially for visual displays.

Finally is also an aromatic glycol ether of the formula (I)

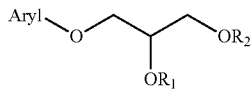

(I)

in which aryl is a substituted or unsubstituted aromatic radical, excluding unsubstituted phenyl, and
$R_1$ and $R_2$ are each independently a radical of the formula (II) or (III)

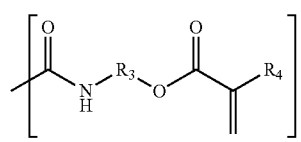

(II)

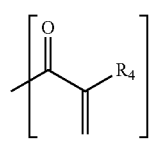

(III)

in which
$R_3$ is an organic radical which has up to 6 carbon atoms and may contain oxygen and/or sulphur atoms,
$R_4$ is a radical selected from the group of —H, —CH$_3$, It is particularly preferred here when aryl is a radical selected from the group of methylphenyl, ethylphenyl, thiomethylphenyl, methoxyphenyl, biphenyl and naphthyl and/or in each case one of the $R_1$ and $R_2$ radicals is a radical of the formula (II) and in each case one of the $R_1$ and $R_2$ radicals is a radical of the formula (III), where $R_3$ may especially be a —CH$_2$CH$_2$— radical.

It is also preferable when aryl radical is substituted by 1 to 5 and preferably 1 to 3 identical or different substituents selected from the group of n-alkyl, branched alkyl, alkyloxy, phenyl, benzyl, phenylalkyl, naphthyl, methylthiyl, ethylthiyl, alkylthiyl, alkylthioalkyl, phenoxy, phenylthiyl, napthylthiyl, fluorine, chlorine, bromine and/or iodine, and preferably by 1 to 3 identical or different substituents selected from the group of methyl, ethyl, thiomethyl, methoxy, phenyl.

EXAMPLES

The invention is illustrated in detail hereinafter by examples.

Figure 2:
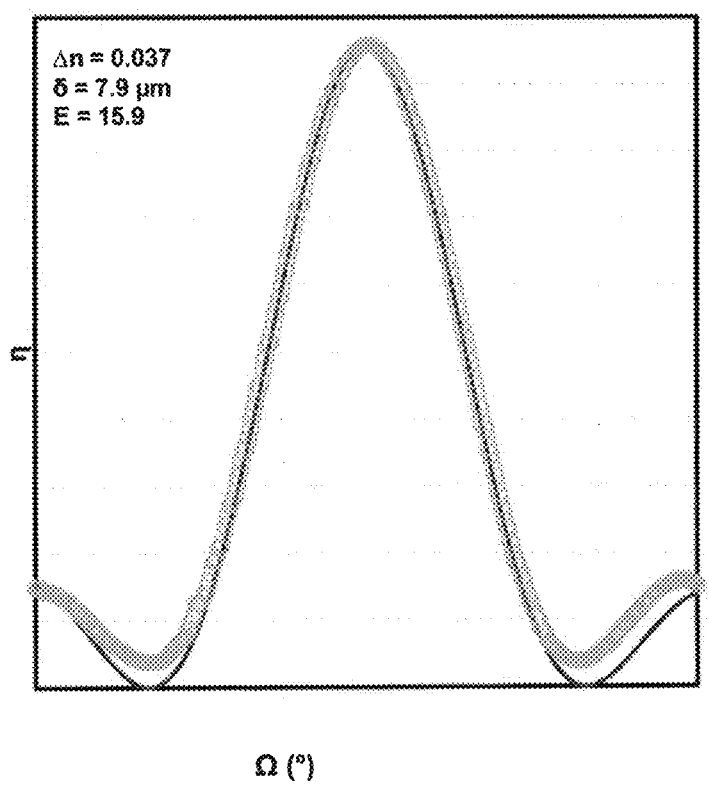

The drawings show:

FIG. 1 the geometry of a holographic media tester (HMT) at λ=532 nm (DPSS 1a-ser=diode pumped solid state laser) and FIG. 2 the measured diffraction efficiency η as circles plotted against the angle detuning ΔΩ and the fit to the Kogelnik theory as a solid line. The figure shows example 4.4.

Figure 3:
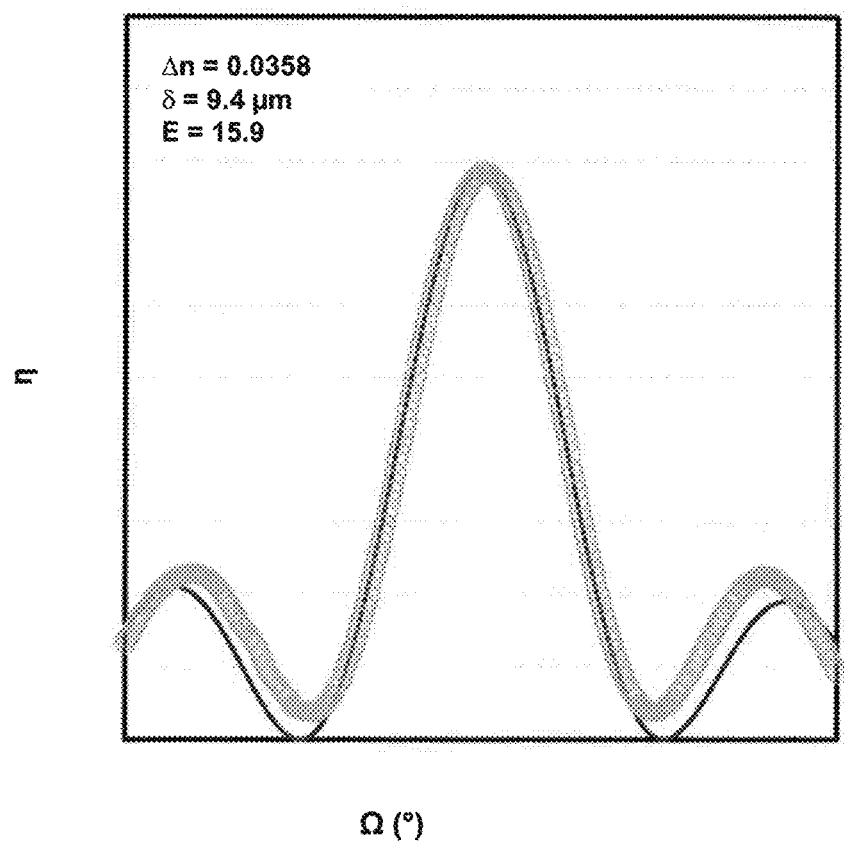

FIG. 3 the measured diffraction efficiency η as circles plotted against the angle detuning ΔΩ and the fit to the Kogelnik theory as a solid line. The figure shows example 4.8.

TEST METHODS

Determination of Viscosity:

Viscosity was determined with a Physica MCR 51 (from Anton Paar) viscometer. For this purpose, the sample was equilibrated and a ball was suspended (for low viscosities η<10 000 mPas: 23° C., ball diameter 25 mm (CP-25) and for high viscosities η>10 000 mPas: 50° C., ball diameter 60 mm (CP-60)). About 0.5-1 g of product was placed onto the plate, and the ball was allowed to drop down, such that the ball was fully wetted with product. Excess product was wiped off. The shear rate (about 500 l/s at lower viscosities and about 100 l/s at higher viscosities) was set automatically by the instrument. 20 measurements were made in each case and the mean was determined.

Determination of Refractive Index:

For high-viscosity and solid products, the refractive index was determined at a wavelength of 589 nm by obtaining the refractive index n from the transmission and reflection spectra as a function of the wavelength of the sample. For this purpose, films of the samples of thickness about 100-300 mm were spun onto quartz glass slides from a five percent by weight solution in ethyl acetate. The transmission and reflection spectrum of this layer assembly was measured with a CD-Measurement System ETA-RT spectrometer from STEAG ETA-Optik, and then the layer thickness and the spectral profile of n were fitted to the measured transmission and reflection spectra. This was done with the spectrometer's internal software and additionally required the n data of the quartz glass substrate, which were determined beforehand in a blank measurement.

For liquid products, an Abbe refractometer was used to determine the refractive index at 589 nm. This was done by applying 3 drops of the product onto the cleaned measurement prism of the instrument, folding down the illumination prism and then equilibrating to 20° C. within 2 minutes. Subsequently, in the observation field, the light/dark boundary was positioned precisely onto the crosshairs of the refractometer. Once there was no longer any variation in the value set, the refractive index was read off on the instrument to four decimal places. A double determination was conducted. Differences of up to 0.0002 scale division were permissible.

Measurement of Haze

Haze was measured to ASTM D 1003. The haze is the percentage of light transmitted which deviates by more than 2.5° on average from the light beam emitted. To measure the haze, the holographic coupons were cleaned on the outside prior to the measurement, in order to avoid distortion of the result by fingerprints and dirt on the glass surfaces. Then the coupons were inserted into a Byk-Gardner Haze-Gard-Plus instrument for analysis. The layer thickness of the coupon was measured as described below in the section "Measurement of the holographic properties DE and Δn of the holographic media by means of twin beam interference in transmission arrangement" in the simulation of the theoretical Bragg curve according to Kogelnik.

Measurement of Time for Dissolution of Writing Monomers 1.47 g of the polyol component were introduced into a tablet tube, a stirrer bar was added and the tablet tube was positioned on a magnetic stirrer. Subsequently, 1.00 g of the writing monomer to be tested was added while stirring and the time taken for a visually clear, homogeneous solution to form was determined.

Isocyanate Content

Reported NCO values (isocyanate contents) were determined to DIN EN ISO 11909.

The full conversion of NCO groups, i.e. the absence thereof, in a reaction mixture was detected by IR spectroscopy. Thus, complete conversion was assumed when no NCO band (2261 cm$^{-1}$) was visible in the IR spectrum of the reaction mixture.

Solids Content

An unpainted tin can lid and a paperclip were used to ascertain the tare weight. Then about 1 g of the sample to be analysed was weighed out and then distributed homogeneously in the tin can lid with the suitably bent paperclip. The paperclip remained in the sample for the measurement. The starting weight was determined, then the assembly was heated in a laboratory oven at 125° C. for 1 hour, and then the final weight was determined. The solids content was determined by the following equation: Final weight [g]*100 starting weight [g]=% by weight of solids.

Measurement of the Holographic Properties DE and Δn of the Holographic Media by Means of Twin Beam Interference in Transmission Arrangement The media produced were tested for their holographic properties by means of a measurement setup according to FIG. 1 as follows:

FIG. 1 shows the holographic test setup with which the diffraction efficiency (DE) of the media was measured, with the following labels: M=mirror, S=shutter, SF=spatial filter, CL=collimator lens, λ/2=λ/2 plate, PBS=polarization-sensitive beam splitter, D=detector, I=iris diaphragm, $\alpha_0$=−22.3°, $\beta_0$=22.3° are the angles of incidence of the coherent beams measured outside the sample (outside the medium). RD=reference direction of the turntable.

The beam of a DPSS laser (emission wavelength 532 nm) was converted to a parallel homogeneous beam with the aid of the spatial filter (SF) and together with the collimation lens (CL). The final cross sections of the signal and reference beam are fixed by the iris diaphragms (I). The diameter of the iris diaphragm opening is 0.4 cm. The polarization-dependent beam splitters (PBS) split the laser beam into two coherent beams of identical polarization. By means of the λ/2 plates, the power of the reference beam was set to 2.0 mW and the power of the signal beam to 2.0 mW. The powers were determined using the semiconductor detectors (D) with the sample removed. The angle of incidence ($\alpha_0$)) of the reference beam is −22.3°; the angle of incidence ($\beta_0$) of the signal beam is 22.3°. The angles are measured proceeding from the sample normal to the beam direction. According to FIG. 1, therefore, $\alpha_0$ has a negative sign and $\beta_0$ a positive sign. At the location of the sample (medium), the interference field of the two overlapping beams produced a pattern of light and dark strips parallel to the angle bisectors of the two beams incident on the sample (transmission hologram). The strip spacing Λ, also called grating period, in the medium is ~700 nm (the refractive index of the medium assumed to be ~1.504).

Holograms were recorded in the medium in the following manner:

Both shutters (S) are opened for the exposure time t.

Thereafter, with the shutters (S) closed, the medium is allowed 5 minutes for the diffusion of the as yet unpolymerized writing monomers.

The holograms recorded were then reconstructed in the following manner. The shutter of the signal beam remained closed. The shutter of the reference beam was opened. The iris diaphragm of the reference beam was closed to a diameter of <1 mm. This ensured that the beam was always completely within the previously recorded hologram for all angles of rotation (Ω) of the medium. The turntable, under computer control, swept over the angle range from $\Omega_{min}$ to $\omega_{max}$ with an angle step width of 0.05°. Ω is measured from the sample normal to the reference direction of the turntable. The reference direction (Ω=0) of the turntable is obtained when the angles of incidence of the reference beam and of the signal beam have the same absolute value on recording of the hologram, i.e. $\alpha_0$=−22.3° and $\beta_0$=22.3°. In general, the following is true of the interference field in the course of writing (recording) of a symmetric transmission hologram ($\alpha_0$=−$\beta_0$):

$$\alpha_0 = \theta_0$$

$\theta_0$ is the semiangle in the laboratory system outside the medium. Thus, in this case, $\theta_0$=−22.3°. At each setting for the angle of rotation Ω, the powers of the beam transmitted in the zeroth order were measured by means of the corresponding detector D, and the powers of the beam diffracted in the first order by means of the detector D. The diffraction efficiency was calculated at each setting of angle Ω as the quotient of:

$$\eta = \frac{P_D}{P_D + P_T}$$

$P_D$ is the power in the detector for the diffracted beam and $P_T$ is the power in the detector for the transmitted beam.

By means of the process described above, the Bragg curve, which describes the diffraction efficiency η as a function of the angle of rotation Ω for the recorded hologram, was measured and saved on a computer. In addition, the intensity transmitted into the zeroth order was also recorded against the angle of rotation Ω and saved on a computer.

The central diffraction efficiency (DE=η0) of the hologram was determined at Ω=0.

The refractive index contrast Δn and the thickness d of the photopolymer layer were now fitted to the measured Bragg curve by means of coupled wave theory (see: H. Kogelnik, The Bell System Technical Journal, Volume 48, November 1969, Number 9 page 2909-page 2947). The evaluation process is described hereinafter:

For the Bragg curve η(Ω) of a transmission hologram, according to Kogelnik:

$$\eta = \frac{\sin^2\left(\sqrt{v^2 + \xi^2}\right)}{1 + \frac{\xi^2}{v^2}} \text{ with:}$$

$$v = \frac{\pi \cdot \Delta n \cdot d}{\lambda \cdot \sqrt{|c_s \cdot c_r|}} \quad \xi = -\frac{d}{2 \cdot c_s} \cdot DP$$

$$c_s = \cos(\vartheta) \quad c_r = \cos(\vartheta)$$

$$DP = \frac{\pi}{\Lambda} \cdot \left(-2 \cdot \sin(\vartheta) - \frac{\lambda}{n \cdot \Lambda}\right)$$

$$\Lambda = -\frac{\pi}{2 \cdot n \cdot \sin(\alpha)}$$

In the reconstruction of the hologram, as explained analogously above:

$$\theta_0 = \theta_0 + \Omega$$

$$\sin(\theta_0) = n \cdot \sin(\theta)$$

Under the Bragg condition, the "dephasing" DP=0. And it follows correspondingly that:

$$\alpha_0 = \theta_0$$

$$\sin(\alpha_0) = n \cdot \sin(\alpha)$$

v is the grating thickness and ξ is the detuning parameter of the refractive index grating which has been recorded. n is the mean refractive index of the photopolymer and was set to 1.504. λ is the wavelength of the laser light in the vacuum.

The central diffraction efficiency (DE=η0), when ξ=0, is then calculated to be:

$$DE = \sin^2(v) = \sin^2\left(\frac{\pi \cdot \Delta n \cdot d}{\lambda \cdot \cos(\alpha)}\right)$$

The measured data for the diffraction efficiency and the theoretical Bragg curve are plotted against the angle of rotation Ω, as shown in FIG. 2 and FIG. 3.

Since DE is known, the shape of the theoretical Bragg curve, according to Kogelnik, is determined only by the thickness d of the photopolymer layer. Δn is corrected via DE for a given thickness d such that measurement and theory for DE are always in agreement. d is thus adjusted until the angle positions of the first secondary minima and the heights of the first secondary maxima of the theoretical Bragg curve correspond to the angle positions of the first secondary minima and the heights of the first secondary maxima of the measured Bragg curve.

FIG. 2 and FIG. 3 show the theoretically calculated Bragg curves η fitted to the experimental data by the coupled wave theory (also called Kogelnik theory) as a solid line, and shows, for comparison, the experimentally determined diffraction efficiency (in circle symbols) plotted against the angle of rotation Ω.

For a formulation, this procedure was repeated, possibly several times, for different exposure times t on different media, in order to find the mean energy dose of the incident laser beam in the course of recording of the hologram at which Δn reaches the saturation value. The mean energy dose E is calculated as follows from the powers of the two component beams assigned to the angles $\alpha_0$ and $\beta_0$ (reference beam where $P_r=2.00$ mW and signal beam where $P_s=2.00$ mW), the exposure time t and the diameter of the iris diaphragm (0.4 cm):

$$E(mJ/cm^2) = \frac{2 \cdot [P_r + P_s] \cdot t(s)}{\pi \cdot 0.4^2 \text{ cm}^2}$$

Chemicals:
In each case, the CAS number, if known, is stated in square brackets.

| | |
|---|---|
| m-Cresol | [108-39-4]—ABCR GmbH & Co KG, Karlsruhe, Germany |
| 3-Ethylphenol | [620-17-7]—Fluka/Sigma-Aldrich Chemie GmbH, Steinheim, Germany |
| 3-(Methylthio)phenol | [1073-29-6]—ABCR GmbH & Co KG, Karlsruhe, Germany |
| 4-(Methylthio)phenol | [1073-72-9]—Sigma-Aldrich Chemie GmbH, Steinheim, Germany |
| Potassium carbonate | Sigma-Aldrich Chemie GmbH, Steinheim Germany |
| Epibromohydrin | [3132-64-7]—Sigma-Aldrich Chemie GmbH, Steinheim, Germany |
| Phenyl glycidyl ether | Denacol EX141; Nagase ChemteX Corporation, Osaka, Japan |
| Triphenylphosphine | [603-35-0] ABCR GmbH & Co KG, Karlsruhe, Germany |
| Acrylic acid | [79-10-7] Acros Organics, Geel, Belgium |
| Methacrylic acid | [79-41-4] Acros Organics, Geel, Belgium |
| Ionol | [128-37-0] Merck KGaA, Darmstadt, Germany |
| 2-[(Biphenyl-2-yloxy)methyl]oxirane | Denacol EX142; Nagase ChemteX Corporation, Osaka, Japan |
| 2-[(2-Methyl-phenoxy)methyl]oxirane | [2210-79-9] Sigma-Aldrich Chemie GMbH, Steinheim, Germany |
| 2-Isocyanatoethyl acrylate | [13641-96-8]—Karen® AOI, SHOWA DENKO K.K., Fine Chemicals Group, Specialty Chemicals Department, Chemicals Division, Japan |
| 2-Isocyanatoethyl methacrylate | [30674-80-7]—Karenz® MOI, SHOWA DENKO K.K., Fine Chemicals Group, Specialty Chemicals Department, Chemicals Division, Japan |
| 1,2-Cyclohexanamino-N,N'-bis (3,5-di-t-butylsalicylidene)cobalt(III) p-toluenesulphonate monohydrate | [672306-06-8] ABCR GmbH & Co KG, Karlsruhe, Germany |
| 1-Isocyanato-3-(methylsulphanyl)benzene | [28479-19-8]—Sigma-Aldrich Chemie GmbH, Steinheim, Germany |
| Tris(p-isocyanatophenyl) thiophosphate | Desmodur® RFE, product from Bayer MaterialScience AG, Leverkusen, Germany |
| Dibutyltin dilaurate | [77-58-7]—urethanization catalyst Desmorapid Z, Bayer MaterialScience AG, Leverkusen, Germany |

-continued

| | |
|---|---|
| Fomrez ® UL 28 | urethanization catalyst, commercial product from Momentive Performance Chemicals, Wilton, CT, USA. |
| Addocat ® SO | a tin-based catalyst from RheinChemie, Mannheim, Germany |
| Desmodur ® N 3900 | product from Bayer MaterialScience AG, Leverkusen, DE, hexane diisocyanate-based polyisocyanate, proportion of iminooxadiazinedione at least 30%, NCO content: 23.5%. |
| CGI-909 | tetrabutylammonium tris(3-chloro-4-methylphenyl)(hexyl)borate [1147315-11-4] is a product from BASF SE (formerly Ciba Inc.). |
| Trimethylhexamethylene diisocyanate | [28679-16-5]—ABCR GmbH & Co KG, Karlsruhe, Germany |
| 1H,1H-7H-Perfluoroheptan-1-ol | [335-99-9]—ABCR GmbH & Co KG, Karlsruhe, Germany |
| Crystal violet | [548-62-9] Sigma-Aldrich Chemie GmbH, Steinheim, Germany |
| Irgacure ® 250 | [344562-80-7], iodonium, (4-methylphenyl)[4-(2-methylpropyl)phenyl]-, hexafluorophosphate(1-) product from BASF SE |

Inventive Writing Monomers:

General Method for Preparation of the Oxiranes (Examples 1.5 to 1.7; Other Oxiranes Used are Commercially Available)

1 equivalent of phenol and 2.4 equivalents of potassium carbonate were initially charged in 2-butanone. Then 3 equivalents of epibromohydrin were added gradually at room temperature. The amount of 2-butanone corresponded to 50 percent by weight of the total amount. There was a preliminary check of whether the phenol dissolves sufficiently in 2-butanone. The potassium carbonate suspension was then boiled under reflux.

Once full conversion had been attained, was checked by $^1$H NMR spectroscopy (see below for statement of time), the potassium carbonate was filtered off and the mixture was concentrated on a rotary evaporator. This gave the liquid, clear products, some of which were coloured, without further workup. The yield based on the phenol used was quantitative.

Example 1.5 2-[(3-methylphenoxy)methyl]oxirane

Reactants: 11.9 g m-cresol
45.2 g epibromohydrin
36.4 g potassium carbonate
93.5 g 2-butanone
Conditions: 16.5 h at 86° C. and 49.5 hours at 70° C.
$^1$H NMR (CDCl$_3$, 400 MHz): δ (1H)=7.18 (t, 1H), 6.77 (d; 1H), 6.68-6.75 (m, 2H), 4.18 (dd, 3.95 (dd, 1H), 3.24 (m, 1H), 2.89 (dd, 1H), 2.73 (dd, 1H), 2.32 (s, 3H).

Example 1.6 2-[(3-ethylphenoxy)methyl]oxirane

Reactants: 12.2 g 3-ethylphenol
41.1 g epibromohydrin
33.1 g potassium carbonate
86.4 g 2-butanone
Conditions: 19.3 h at 86° C. and 50 hours at 70° C.
$^1$H NMR (CDCl$_3$, 400 MHz): δ (1H)=7.40 (t, 1H), 6.80 (dd, 1H), 6.77 (m, 2H), 6.70 (dd, 1H), 4.40 (dd, 1H), 3.95 (dd, 1H), 3.35 (m, 1H), 2.85 (dd, 1H), 2.75 (dd, 1H), 2.65 (q, 2H), 1.25 (t, 3H).

Example 1.7 2-{[4-(methylsulphanyl)phenoxy]methyl}oxirane

Reactants: 15.4 g 4-(methylthio)phenol
45.2 g epibromohydrin
36.4 g potassium carbonate
97.1 g 2-butanone
Conditions: 16.3 h at 86° C. and 50.2 hours at 70° C.
$^1$H NMR (CDCl$_3$, 400 MHz): δ (1H)=7.25 (<u>AA</u>'BB', 2H), 6.88 (AA'<u>BB</u>', 2H), 4.20 (dd, 1H), 3.90 (dd, 1H), 3.40 (m, 1H), 2.85 (dd, 1H), 2.73 (dd, 1H), 2.40 (s, 3H).

General Method for Preparation of the (Meth)Acrylic Acid-Oxirane Adducts (Examples 2.1-2.11)

The oxirane, the catalyst, stabilizer and the (meth)acrylic acid were initially charged in a three-neck flask equipped with precision glass stirrer and stirrer motor, and also a drying tube. The mixture was heated to 90° C., and stirring was continued at this temperature until, in the $^1$H NMR spectrum, a conversion of the oxirane group of >95% was apparent or no oxirane groups were detectable any longer. (MC=main components, SC=secondary component)

Example 2.1+2.2 Mixture of 2-hydroxy-3-phenoxypropyl acrylate and 1-hydroxy-3-phenoxypropan-2-yl acrylate (about 85:15)

Reactants: 75.3 g phenyl glycidyl ether (Denacol EX141)
328 mg triphenylphosphine
36.0 acrylic acid
1.1 mg ionol
Conditions: Reaction time 37 hours
A clear, colourless, viscous liquid was obtained.
$^1$H NMR (CDCl$_3$, 400 MHz): δ (1H)=7.23-7.32 (m, 2H), 6.92-7.00 (m, 1H), 6.84-6.92 (m, 2H), 6.46 (d, 1H), 6.16 (dd, 1H), 5.97 (d, 1H), 5.28 (p, 1H from SC), 3.9-4.45 (m, 5H), 2.72 (t, 1H from SC, OH), 2.60 (s, broad, 1H, OH).

Example 2.3 Mixture of 2-hydroxy-3-phenoxypropyl methacrylate and 1-hydroxy-3-phenoxypropan-2-yl methacrylate (about 85:15)

Reactants: 37.7 g phenyl glycidyl ether (Denacol EX141)
164 mg triphenylphosphine
21.5 g methacrylic acid
0.6 mg ionol
Conditions: Reaction time 34.5 hours
A clear, colourless, viscous liquid was obtained.

¹H NMR (CDCl₃, 400 MHz): δ (1H)=7.25-7.32 (m, 2H), 6.96 (t, 1H), 6.91 (d, 2H), 6.14 (s, 1H), 5.60 (s, 1H), 5.28 (p, 1H from SC), 3.35 (in, 2H from MC), 4.29 (p, 1H from MC), 4.20 (d, 2H from SC), 4.0-4.1 (m, 2H from MC), 3.94 (m, 2H from SC), 2.69 (s, broad, 1H, OH), 1.95 (s, 3H).

Example 2.4 Mixture of 2-hydroxy-3-(2-methylphenoxy)propyl acrylate and 1-hydroxy-3-(2-methylphenoxy)propan-2-yl acrylate (about 85:15)

Reactants: 16.4 g 2-[(2-methylphenoxy)methyl]oxirane
66 mg triphenylphosphine
7.2 g acrylic acid
11.8 mg ionol
Conditions: Reaction time 17 hours
A clear, colourless, viscous liquid was obtained.
¹H NMR (CDCl₃, 400 MHz): δ (1H) 7.1-7.2 (m, 2H), 6.88 (t, 1H), 6.80 (d, 1H), 6.44 (d, 1H), 6.18 (dd, 1H), 5.88 (d, 1H), 5.32 (p, 1H from SC), 4.35-4.45 (m, 2H from MC), 4.29 (p, 1H from MC), 4.19 (d, 2H from SC), 4.0-4.1 (m, 2H from MC), 3.96 (m, 2H from SC), 2.93 (s, broad, 1H, OH), 2.22 (s, 3H from MC), 2.20 (s, 3H, from SC).

Example 2.5 Mixture of 2-hydroxy-3-(3-methylphenoxy)propyl acrylate and 1-hydroxy-3-(3-methylphenoxy)propan-2-yl acrylate (about 85:15)

Reactants: 16.5 g Example 1.5
66 mg triphenylphosphine
7.3 g acrylic acid
11.9 mg ionol
Conditions: Reaction time 17 hours
A clear, colourless, viscous liquid was obtained.
¹H NMR (CDCl₃, 400 MHz): δ (1H)=7.13-7.20 (t, 1H), 6.78 (d, 1H), 6.68-6.75 (m, 2H), 6.45 (d, 1H), 6.18 (dd, 1H), 5.87 (d, 1H), 5.28 (p, 1H from SC), 4.3-4.4 (m, 2H from MC), 4.28 (p, 1H from MC), 4.15-4.25 (m, 2H from SC), 3.98-4.08 (m, 2H from MC), 3.94 (m, 2H from SC), 2.90 (s, broad, 1H, OH), 2.30 (s, 3H).

Example 2.6 Mixture of 2-hydroxy-3-(3-ethylphenoxy)propyl acrylate and 1-hydroxy-3-(3-ethylphenoxy)propan-2-yl acrylate (about 85:15)

Reactants: 15.3 g Example 1.6
56 mg triphenylphosphine
6.2 g acrylic acid
10.8 mg ionol
Conditions: Reaction time 17 hours
A clear, colourless, viscous liquid was obtained.
¹H NMR (CDCl₃, 400 MHz): δ (1H)=7.13-7.20 (m, 1H), 6.80 (d, 1H), 6.75 (s, 1H), 6.71 (dd, 1H), 6.45 (d, 1H), 6.18 (dd, 1H), 5.85 (d, 1H), 5.28 (p, 1H from SC), 4.3-4.4 (m, 2H from MC), 4.25 (p, 1H from MC), 4.19 (d, 2H from SC), 3.99-4.07 (m, 2H from MC), 3.93 (d, 2H from SC), 3.35 (s, broad, 1H, OH), 2.60 (q, 2H), 1.21 (t, 3H).

Example 2.7 Mixture of 2-hydroxy-3-[4-(methylsulphanyl)phenoxy]propyl acrylate and 1-hydroxy-3-[4-(methylsulphanyl)phenoxy]propan-2-yl acrylate (about 85:15)

Reactants: 35.7 g Example 1.7
119 mg triphenylphosphine
13.1 g acrylic acid
24.4 mg ionol
Conditions: Reaction time 39 hours at 70° C.
GC-MS (EI) Retention time (from acetonitrile solution, only all the secondary components that appear >10% relative to the main component in the GC are mentioned):
1. 100%: 17.59 min (MS-EI: m/e=55, 125, 129, 140, 268): isomeric main products (M=268)
2. 17.8%: 3.03 min (MS-EI: m/e=27, 45, 55, 72) acrylic acid (M=72)
3. 11.2%: 21.30 min (MS-EI: m/e=55, 57, 115, 129, 353, 382) 3-({4-[3-(acryloyloxy)-2-hydroxypropoxy]phenyl}sulphanyl)-2-hydroxypropyl acrylate (M=382)

Example 2.8 Mixture of 3-(biphenyl-2-yloxy)-2-hydroxypropyl acrylate and 1-(biphenyl-2-yloxy)-3-hydroxypropan-2-yl acrylate (about 85:15)

Reactants: 191.2 g 2-[(biphenyl-2-yloxy)methyl]oxirane (Denacol EX 142)
0.525 g triphenylphosphine
57.6 g acrylic acid
2.5 ionol
Conditions: Reaction time 24.5 hours at 90° C.
A clear, colourless, viscous liquid was obtained.
¹H NMR (CDCl₃, 400 MHz): δ (1H)=7.45 (d, 2H), 7.38 (t, 2H), 7.2-7.35 (m, 3H), 7.15 (t, 2H), 6.96 (d, 2H), 6.37 (dd, 1H), 6.13 (dd, 1H), 5.81 (d, 1H), 5.28 (p, 1H from SC), 4.37 (t, 1H from SC, OH), 4.28-4.35 (m, 2H), 4.15 (m, 2H from MC), 4.13 (p, 1H), 3.95-4.06 (m, 2H), 3.75 (m, 2H from SC), 2.74 (s, broad, 1H, OH).
GC-MS 1.1% acrylic acid, 7.8% 2-[(biphenyl-2-yloxy)methyl]oxirane (reactant), 1.5% reactant+HCl, 2.7% reactant+H2O, 73.2% products (isomers), 2.2% product+acrylic acid, 2.7% reactant+biphenylphenol, 3.3% product+reactant Example 2.9 Mixture of 2-hydroxy-3-(1-naphthyloxy)propyl acrylate and 1-hydroxy-3-(1-naphthyloxy)propan-2-yl acrylate (about 85:15)

Reactants: 46.0 g 2-[(1-naphthyloxy)methyl]oxirane
0.151 g triphenylphosphine
16.6 g acrylic acid
0.6 mg ionol
Conditions: Reaction time 22.7 hours
A clear, colourless, viscous liquid was obtained.

¹H NMR (CDCl₃, 400 MHz): δ (1H)=8.18-8.25 (m, 1H), 7.73-7.80 (m, 1H), 7.38-7.49 (m, 3H), 7.29-7.35 (2×t, 1H), 6.76 (d, 1H), 6.44 (2×d, 1H), 6.15 (2×dd, 1H), 5.82 (d, 1H), 5.43 (p, 1H from SC), 4.35-4.50 (m, 3H from MC), 4.30 (d, 2H from SC), 4.13-4.18 (m, 2H from MC), 3.98 (d, 2H from SC), 3.32 (s, broad, 1H, OH), 2.70 (t, 1H from SC, OH).

Example 2.10 Mixture of 2-hydroxy-3-(2-methoxyphenoxy)propyl acrylate and 1-hydroxy-3-(2-methoxyphenoxy)propan-2-yl acrylate (about 85:15)

Reactants: 10.8 g 1,2-epoxy-3-(2-methoxyphenoxy)propane
0.039 g triphenylphosphine
4.3 g acrylic acid
7.6 mg ionol
Conditions: Reaction time 29.3 hours
A clear, colourless, viscous liquid was obtained.

¹H NMR (CDCl₃, 400 MHz): δ (1H)=6.82-7.01 (m, 4H), 6.44 (2×d, 1H), 6.15 (2×dd, 1H), 5.82 (d, 1H), 5.28 (p, 1H from SC), 4.30-4.42 (m, 2H from MC), 4.27 (m, 1H from MC), 4.12 (dd, from MC, <u>A</u>BX), 4.04 (dd, 1H from MC, A B<u>X</u>), 3.98 (d, 2H from SC), 3.78-3.85 (m, 3H, O–Me from MC and from SC+2H from SC), 3.21 (s, broad, 1H, OH).

Example 2.11 2-Hydroxy-3-phenoxypropyl acrylate

Reactants: 8.3 g phenyl glycidyl ether
0.030 g 1,2-cyclohexanamino-N,N'-bis (3,5-di-t-butyl-salicylidene)cobalt(III) p-toluenesulphonate monohydrate
3.9 g acrylic acid
0.1 mg ionol
Conditions: Reaction time 40 hours at room temperature
Workup: 5 g of the crude product were diluted with 25 g of a mixture of butyl acetate and toluene and then freed of the cobalt catalyst by means of a gravity column and, with addition of 0.005 mg of ionol, freed of the solvent mixture in a rotary evaporator.
¹H NMR (CDCl₃, 400 MHz): δ (1H) 7.28 (m, 2H), 6.98 (tt, 1H), 6.92 (dd, 2H), 6.46 (dd, 1H), 6.17 (dd, 1H), 5.87 (dd, 1H), 4.32-4.42 (m, 2H), 4.28 (m, 1H), 4.00-4.09 (m, 2H), 2.65 (d, 1H, OH). Purity by NMR>92%.

General Method for Preparation of the Inventive Aromatic Glycol Ether Writing Monomers (Examples 3.1-3.11)

The precursor (Example 2.1-2.11), dibutyltin dilaurate and 2,6-di-tert-butyl-4-methylphenol were initially charged in a three-neck flask which was equipped with a precision glass stirrer and stirrer motor, gas inlet and drying tube. Subsequently, the mixture was heated to 60° C., air was passed over slowly, and the 2-isocyanatoethyl (meth)acrylate was added dropwise while stirring within about half an hour. Stirring was continued until it was no longer possible to observe any NCO band (2261 cm⁻¹) in the IR spectrum. Table 1 shows details of the reaction conditions and the characterization of the inventive writing monomers:

TABLE 1

Preparation conditions and characterizations of the inventive writing monomers

| Example | Reactant 1 | Reactant 2 | DBTL | Ionol | Temp | Reaction time | Viscosity | Product appearance | Fingerprint (IR, strong, cm⁻¹) |
|---|---|---|---|---|---|---|---|---|---|
| 3.1 | 33.4 g Example 2.1 | 21.2 g AOI | 27 mg | 27 mg | 60° C. | 4.5 h | 6350 mPas | clear, yellowish | 984, 888, 810, 757, 693 |
| 3.2 | 33.4 g Example 2.2 | 23.3 g MOI | 28 mg | 28 mg | 60° C. | 3.7 h | 4630 mPas | clear, yellow | 985, 948, 887, 811, 756, 693 |
| 3.3 | 58.2 g Example 2.3 | 38.8 g MOI | 49 mg | 49 mg | 60° C. | 4.7 h | 3830 mPas | clear, orange-brown | 945, 887, 815, 756, 693 |
| 3.4 | 23.6 g Example 2.4 | 14.1 g AOI | 19 Mg/m3 | 19 mg | 60° C. | 9.2 h | 8790 mPas | clear, colourless | 983, 808, 751 |
| 3.5 | 23.6 g Example 2.5 | 14.1 g AOI | 19 mg | 19 mg | 60° C. | 15.5 h | 5150 mPas | clear, amber | 989, 809, 777 |
| 3.6 | 21.5 g Example 2.6 | 12.1 g AOI | 17 mg | 17 mg | 60° C. | 15.5 h | 2670 mPas | clear, amber | 984, 814, 778 |
| 3.7 | 25.2 g Example 2.7 | 13.3 g AOI | 19 mg | 19 mg | 60° C. | 19.5 h | 174700 mPas | clear, yellowish | 987, 812, 775 |
| 3.8 | 140.7 g Example 2.8 | 62.6 g AOI | 102 mg | 102 mg | 60° C. | 13.5 h | 240000 mPas | clear, colourless | 984, 826, 809, 756, 734, 701, 667 |
| 3.9 | 54.5 g Example 2.9 | 28.2 g AOI | — | — | 60° C. | 21.5 h | 176000 mPas | clear, red brown | 984, 809, 794, 773, 738 |
| 3.10 | 15.1 g Example 2.10 | 8.4 g AOI | 12 mg | 12 mg | 60° C. | 14 h | 13190 mPas | clear, colourless | 988, 811 |
| 3.11 | 12.2 g Example 2.11 | 7.7 g AOI | 10 mg | 10 mg | 60° C. | 103 h | 2640 mPas | clear, colourless | 978, 814, 756 |

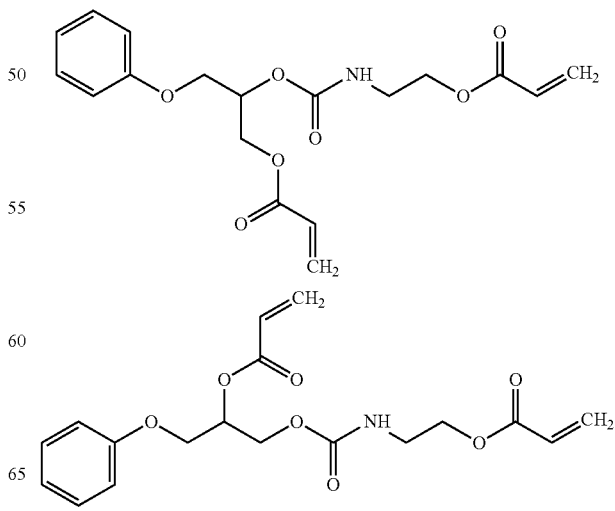

Example 3.1

Example 3.2
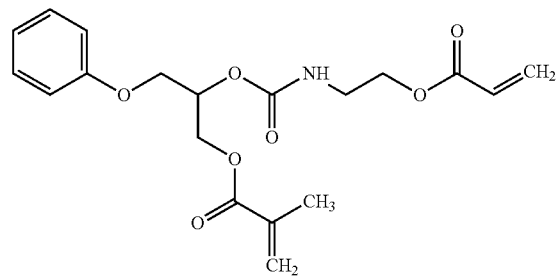
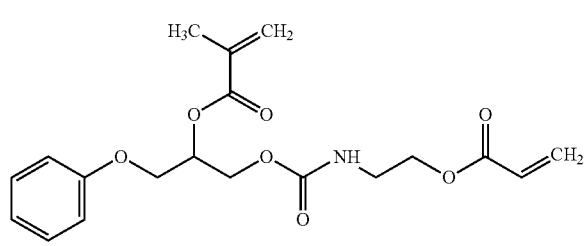
Example 3.3
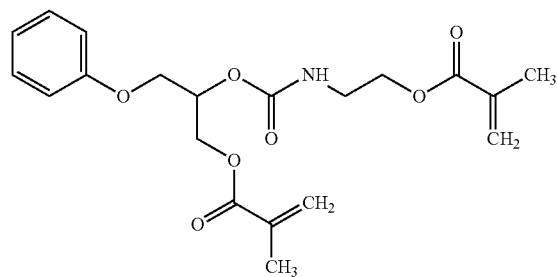
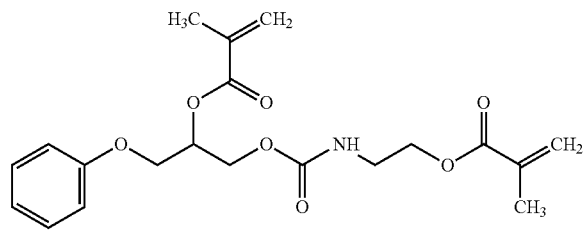
Example 3.4
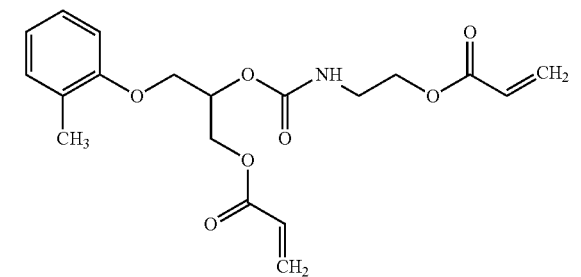
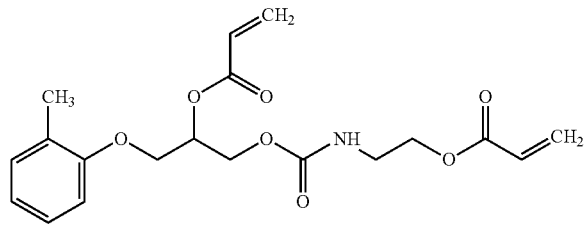
Example 3.5
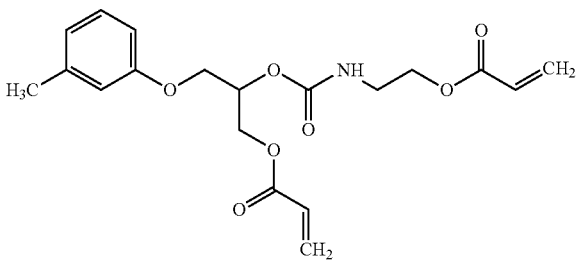
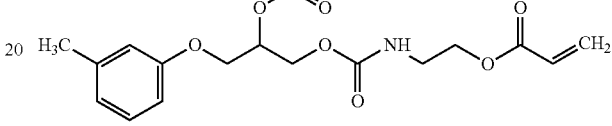
Example 3.6
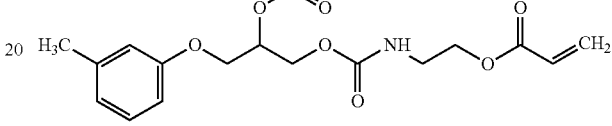
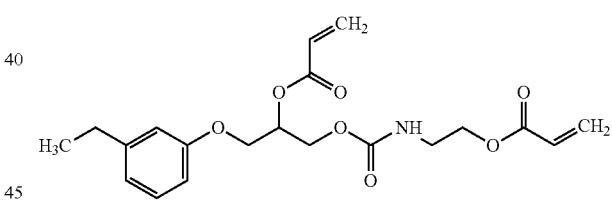
Example 3.7
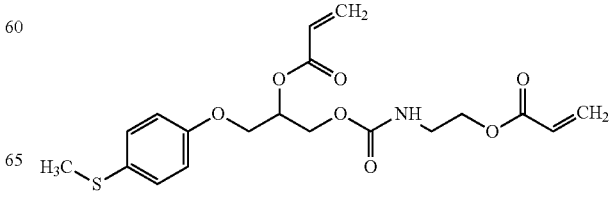

Example 3.8

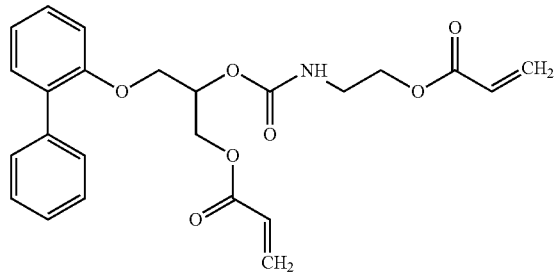

Example 3.11

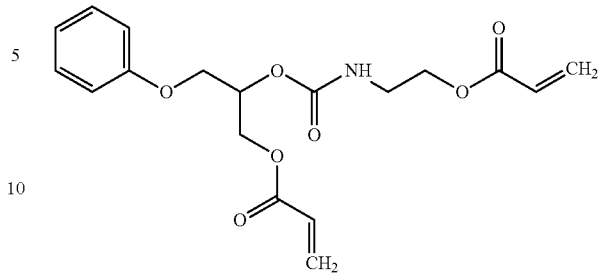

Example 3.9

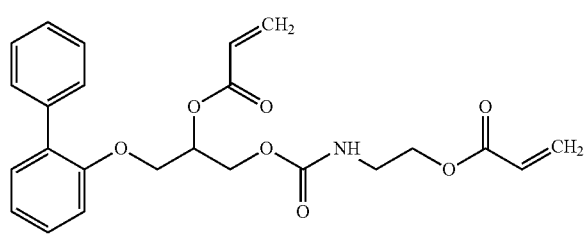

Example 3.10

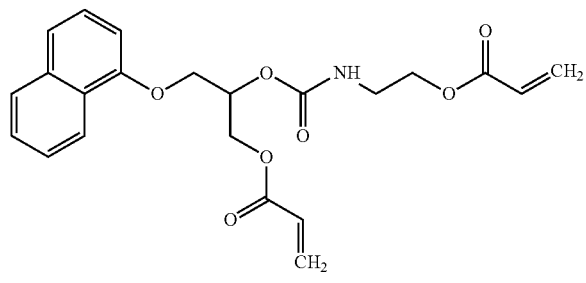

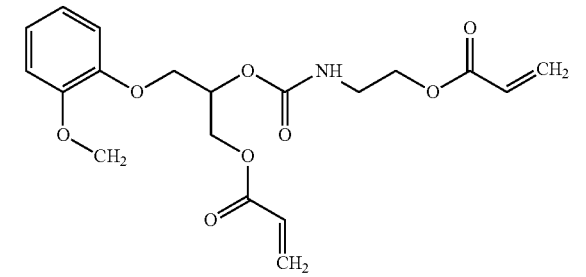

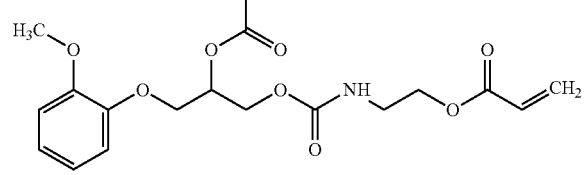

Comparative Example C1: Phosphorothioyltris(oxybenzene-4,1-diylcarbamoyloxyethane-2,1-diyl) trisacrylate [1072455-04-9]

A 500 mL round-bottom flask was initially charged with 0.1 g of 2,6-di-tert-butyl-4-methylphenol, 0.05 g of dibutyltin dilaurate and and 213.07 g of a 27% solution of tris(p-isocyanatophenyl) thiophosphate in ethyl acetate, which were heated to 60° C. Subsequently, 42.37 g of 2-hydroxyethyl acrylate were added dropwise and the mixture was still kept at 60° C. until the isocyanate content had fallen below 0.1%. This was followed by cooling and complete removal of the ethyl acetate under reduced pressure. The product was obtained as a semicrystalline solid. The product obtained has an $n^D{}_{20}$=1.5430 (589 nm).

Comparative Example C2: Benzene-1,3-diylbis [oxy-3-(biphenyl-4-yloxy)propan-1,2-diyl]bisacrylate Comparative example 2 is prepared in a first stage from a dithiol and an oxirane (cf. also Example 4a+b in WO 2012/020061 A1).

The oxirane and the catalyst were initially charged in a three-neck flask equipped with precision glass stirrer and stirrer motor, and also a drying tube. The mixture was heated to 60 to 80° C. and then the dithiol was added dropwise. Subsequently, stirring was continued at the temperature specified until, in the $^1$H NMR spectrum, a conversion of the oxirane group of >95% was apparent or no oxirane groups were detectable any longer.

Stage 1 3,3'-(Butane-2,3-diyldisulphanediyl)bis[1-(biphenyl-2-yloxy)propan-2-ol]

Reactants: 14.3 g 2-[(biphenyl-2-yloxy)methyl]oxirane (Denacol EX 142)
36 mg 1-butyl-3-methylimidazolium bromide
3.7 g 2,3-butanedithiol
Conditions: Reaction temperature 60° C. on dropwise addition, 80° C., reaction time 48.5 h
A clear, colourless, viscous liquid was obtained.
$^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 4.05 (d, 2H), 3.95 (m, 1H), 2.65 (dd, 1H), 2.58 (dd, 1H), 2.4-2.55 (m, 2H), 1.5-4.65 (m, 2H).

Stage 2: 6,13-Bis[(biphenyl-2-yloxy)methyl]-9,10-dimethyl-4,15,20-trioxo-5,14,19-trioxa-8,11-dithia-3,16-diazadocos-21-en-1-yl acrylate Stage 1, dibutyltin dilaurate and 2,6-di-tert-butyl-4-methylphenol were initially charged in a three-neck flask which was equipped with a precision glass stirrer and stirrer motor, gas inlet and drying tube. Subsequently, the mixture was heated to 60° C., air was passed over slowly, and the 2-isocyanatoethyl acrylate was added dropwise within about half an hour. Stirring was continued until it was no longer possible to observe any NCO band (2261 cm$^{-1}$) in the IR spectrum.

Reactants: 18.0 g product from Stage 1
8.5 g 2-isocyanatoethyl acrylate
13 mg dibutyltin dilaurate
3 mg 2,6-di-tert-butyl-4-methylphenol Conditions: dropwise addition (exothermic!) in 35 minutes at 60° C., then reaction time of 16 h at 60° C.

A clear, almost colourless product of high viscosity was obtained.

$n^{20}{}_D$ 1.5840 (589 nm)

Comparative Examples C3-C5

Comparative Examples 4-6 were produced analogously to Comparative Example 3 from WO 2012/020061A1, and the viscosity thereof was measured. The results are shown in Table 2.

TABLE 2

Noninventive Comparative Examples 4-6

| Comparative Example | Noninventive Compound | Example from WO 2012/020061 A1 | Viscosity |
|---|---|---|---|
| C3 | 6,16-Bis[(biphenyl-2-yloxy) methyl]-4,18,23-trioxo-5,11,17,22-tetraoxa-8,14-dithia-3,19-diazapentacos-24-en-1-yl acrylate | 6b | >1 000 000 mPas |
| C4 | 6,13-Bis[(biphenyl-2-yloxy) methyl]-4,15,20-trioxo-10-[({[2-(phenylsulphanyl)phenyl] carbamoyl}oxy)methyl]-5,14,19-trioxa- 8,11-dithia-3,16-diazadocos-21-en-1-yl acrylate | 10b | >1 000 000 mPas |
| C5 | 6,19-Bis[(bipbenyl-2-yloxy) methyl]-4,21,26-trioxo-5,11,14,20,25-pentaoxa-8,17-dithia-3,22-diazaoctacos-27-en-1-yl acrylate | 7b | >1 000 000 mPas |

Polyol Component:

A 1 l flask was initially charged with 0.18 g of Addocat® SO, 374.8 g of ϵ-caprolactone and 374.8 g of a difunctional polytetrahydrofuran polyether polyol (equivalent weight 650 g/mol OH), which were heated to 120° C. and kept at this temperature until the solids content (proportion of nonvolatile constituents) was 99.5% by weight or higher. Subsequently, the mixture was cooled and the product was obtained as a waxy solid.

Urethane acrylate 1: 2-({[3-(Methylsulphanyl)phenyl]carbamoyl}oxy)ethyl prop-2-enoate A 100 ml round-bottom flask was initially charged with 0.02 g of 2,6-di-tert-butyl-4-methylphenol, 0.01 g of Desmorapid® Z, 11.7 g of 3-(methylthio)phenyl isocyanate, and the mixture was heated to 60° C. Subsequently, 8.2 g of 2-hydroxyethyl acrylate were added dropwise and the mixture was still kept at 60° C. until the isocyanate content had fallen below 0.1%. This was followed by cooling. The product was obtained as a colourless liquid.

Fluorinated urethane: Bis(2,2,3,3,4,4,5,5,6,6,7,7-dodecafluoroheptyl)-(2,2,4-trimethylhexane-1,6-diyl) biscarbamate A 6 l round-bottom flask was initially charged with 0.50 g of Desmorapid Z and 1200 g of trimethylhexamethylene diisocyanate, and the mixture was heated to 80° C. Subsequently, 3798 g of 1H,1H,7H-perfluoroheptan-1-ol were added dropwise and the mixture was still kept at 80° C. until the isocyanate content had fallen below 0.1%. This was followed by cooling. The product was obtained as a colourless oil.

Production of the Inventive and Noninventive Media (Coupons) (Examples 4.1 to 4.11 and Comparative Examples C4.1-C4.5)

2.940 g of the above-described polyol component were mixed with 2.000 g of the respective writing monomer (Examples 3.1 to 3.11 and Comparative Examples C4.1-C4.5), 2.000 g of the above-described urethane acrylate 1, 2.000 g of the above-described fluorinated urethane, 0.15 g of CGI 909, 15 mg of crystal violet, 15 mg of Irgacure 250, 15 mg of glass beads of size 9.18 µm and 0.517 g of N-ethylpyrrolidone, so as to obtain a clear (in some cases slightly hazy) solution. This was followed by cooling to 30° C., admixture of 545 mg of Desmodur® N 3900 and renewed mixing. This was finally followed by admixture of 6 mg of Fomrez UL 28 and renewed brief mixing. The resulting liquid mixture was then applied to a glass slide (from Corning, N.Y. 14831, USA, Micro slide plane: thickness 0.96-1.06 mm, 75 mm×50 mm, type: 2947-75×50) and covered with a second glass slide thereon. This test specimen was stored at room temperature for 12 hours and cured in the process. Subsequently, the media were packaged with exclusion of light.

Determination of the Physical Data of the Inventive and Noninventive Media

The measurement of the holographic properties DE and Δn was conducted by the process described above in the "Test methods" section.

The measurement of haze was likewise conducted by the process described above in the "Test methods" section, except that the measurement was preceded by bleaching of the respective medium initially at room temperature under ambient light for about 15-30 minutes until the colour was no longer visually perceptible.

The results of the measurements are shown in Table 3.

TABLE 3

Holographic and optical performance of the inventive examples of the photopolymer formulations 4.1-4.11 and of the comparative examples C4.1 to C4.5

| Inventive Examples | Writing monomer | Dissolution time [min] | Δn at 16 mJ/cm$^2$ [-] | d [µm] | Haze in % [%] |
|---|---|---|---|---|---|
| 4.1 | 3.1 | 0.50 | 0.0310 | 9.6 | 0.6 |
| 4.2 | 3.2 | 0.50 | 0.0275 | 10.8 | 0.7 |
| 4.3 | 3.3 | 0.33 | 0.0278 | 10.2 | 0.9 |
| 4.4 | 3.4 | 0.50 | 0.0370 | 7.9 | 0.4 |
| 4.5 | 3.5 | 1.00 | 0.0250 | 12.0 | 0.8 |
| 4.6 | 3.6 | 0.75 | 0.0250 | 10.7 | 2.0 |
| 4.7 | 3.7 | 2.00 | 0.0265 | 10.8 | 0.9 |

TABLE 3-continued

Holographic and optical performance of the inventive
examples of the photopolymer formulations 4.1-4.11 and of
the comparative examples C4.1 to C4.5

| Inventive Examples | Writing monomer | Dissolution time [min] | Δn at 16 mJ/cm² [-] | d [μm] | Haze in % [%] |
|---|---|---|---|---|---|
| 4.8 | 3.8 | 2.00 | 0.0358 | 9.4 | 1.1 |
| 4.9 | 3.9 | 0.50 | 0.0365 | 11.2 | 0.9 |
| 4.10 | 3.10 | 0.75 | 0.0310 | 11.8 | 0.6 |
| 4.11 | 3.11 | 0.75 | 0.0300 | 6.5 | 1.4 |
| Comparative Examples | | | | | |
| C4.1 | C1 | >2800 | 0.0240 | 9.2 | 54.9 |
| C4.2 | C2 | 480 | 0.0315 | 10.0 | 1.0 |
| C4.3 | C3 | 70 | 0.0292 | 12.2 | 1.4 |
| C4.4 | C4 | >480 | 0.0280 | 13.7 | 3.5 |
| C4.5 | C5 | 25 | 0.0290 | 10.0 | 0.9 |

As apparent from Table 3, the holographic media consisting of inventive formulations comprising a writing monomer of formula (1) exhibited comparable or better holographic performance for transmission holograms of more than Δn>0.02. Furthermore, the inventive examples are suitable for production of low-haze holographic media and, at layer thicknesses greater than 6 μm, exhibit a haze of less than 5%. In Inventive Examples 4.1-4.11, the writing monomers dissolve quickly and easily without addition of solvents within much less than 5 minutes, whereas the writing monomers of Comparative Examples C1-C5 took much longer to dissolve completely. Consequently, the production of the photopolymer formulations is as much more time-consuming in the comparative examples.

The invention claimed is:

1. A photopolymer formulation comprising
D) as writing monomer at least one aromatic glycol ether of the general formula (I)

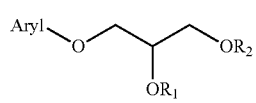

in which Aryl is a substituted aromatic radical,
wherein R1 is a radical of formula (II) and R2 is a radical of formula (III), or
wherein R1 is a radical of formula (III) and R2 is a radical of formula (II)

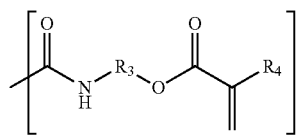

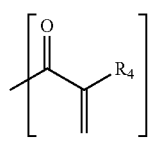

in which
R3 is an organic radical which has up to 6 carbon atoms and may contain oxygen and/or sulphur atoms, and R4 is a radical selected from the group of —H, —CH3;
E) matrix polymers;
F) a photoinitiator, and
wherein the Aryl radical is substituted by 1 to 5 identical or different substituents selected from the group consisting of n-alkyl, branched alkyl, alkyloxy, phenyl, methylphenyl, ethylphenyl, thiomethylphenyl, methoxyphenyl, biphenyl, benzyl, phenylalkyl, naphthyl, methylthiyl, ethylthiyl, alkylthiyl, alkylthioalkyl, phenoxy, phenylthiyl, napthylthiyl, fluorine, chlorine, bromine and iodine.

2. The photopolymer formulation according to claim 1, wherein the Aryl radical comprises 5 to 21 carbon atoms and/or heteroatoms in the aromatic system.

3. The photopolymer formulation claim 1, wherein the Aryl radical is selected from the group consisting of phenyl, methylphenyl, ethylphenyl, thiomethylphenyl, methoxyphenyl, biphenyl and naphthyl.

4. The photopolymer formulation according to claim 1, wherein R3 is a radical selected from the group consisting of —CH2—, —CH2CH2—, —CH(CH3)CH2—, —CH2CH(CH3)—, —CH2CH2CH2—, —CH2CH2CH2CH2—, —CH2CHOCH2CH2—, —CH2CH2OCH2CH2OCH2CH2—.

5. The photopolymer formulation according to claim 1, wherein the R1 radical is a radical of the formula (II) and the R2 radical is a radical of the formula (III), where the R3 radical is a —CH2CH2— radical.

6. The photopolymer formulation according to claim 1, wherein the R1 radical is a radical of the formula (III) and the R2 radical is a radical of the formula (II), where the R3 radical is a —CH2CH2— radical.

7. The photopolymer formulation according to claim 1, wherein the matrix polymers B) have been crosslinked.

8. The photopolymer formulation according to claim 1, wherein the matrix polymers are polyurethanes.

9. The photopolymer formulation according to claim 1, wherein it additionally comprises a monomeric fluoroethane.

10. The photopolymer formulation according to claim 9, wherein the fluorourethane comprise at least one compound of the formula (IV)

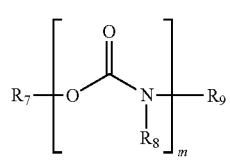

in which m≥1 and m≤8 and R7, R8, R9 are each independently hydrogen or linear, branched, cyclic or heterocyclic organic radicals which are unsubstituted or else optionally substituted by heteroatoms, where preferably at least one of the R7, R8, R9 radicals is substituted by at least one fluorine atom and, more preferably, R7 is an organic radical having at least one fluorine atom.

11. A holographic medium comprising the photopolymer formulation according to claim 1.

12. The holographic medium according to claim 11 into which at least one hologram has been exposed.

13. The holographic medium according to claim 12, wherein the hologram is a reflection, transmission, in-line, off-axis, full-aperture transfer, white light transmission, Denisyuk, off-axis reflection or edge-lit hologram, or else a holographic stereogram, preferably a reflection, transmission or edge-lit hologram.

14. A visual display comprising a holographic medium according to claim 12.

15. The holographic medium according to claim 12 which is applied to chip cards, identification documents, 3D images, product protection labels, labels, banknotes, holographic optical elements, or visual displays.

* * * * *